United States Patent
Patel et al.

(10) Patent No.: US 6,777,082 B2
(45) Date of Patent: Aug. 17, 2004

(54) HYDROGENATED BLOCK COPOLYMERS HAVING ELASTICITY AND ARTICLES MADE THEREFROM

(75) Inventors: Rajen M. Patel, Lake Jackson, TX (US); Pak-Wing S. Chum, Lake Jackson, TX (US); Stephen F. Hahn, Midland, MI (US); Leonie K. Walsh, Houston, TX (US); Rexford A. Maugans, Lake Jackson, TX (US); Selim Bensason, Houston, TX (US); Thoi H. Ho, Lake Jackson, TX (US); Calvin P. Esneault, Baton Rouge, LA (US)

(73) Assignee: The Dow Chemical Company, Midland, MI (US)

(*) Notice: Subject to any disclaimer, the term of this patent is extended or adjusted under 35 U.S.C. 154(b) by 0 days.

(21) Appl. No.: 10/006,082

(22) Filed: Dec. 6, 2001

(65) Prior Publication Data

US 2002/0147273 A1 Oct. 10, 2002

Related U.S. Application Data

(63) Continuation-in-part of application No. 09/627,727, filed on Jul. 28, 2000, now abandoned.
(60) Provisional application No. 60/146,008, filed on Jul. 28, 1999, provisional application No. 60/197,161, filed on Apr. 13, 2000, and provisional application No. 60/203,558, filed on May 11, 2000.

(51) Int. Cl.$^7$ ................................................. C08L 53/00
(52) U.S. Cl. ....................... 428/364; 428/365; 428/375; 525/88; 525/92 R; 525/92 C; 525/89; 525/93; 525/98; 525/99
(58) Field of Search .............................. 428/364, 365, 428/375, 357, 378, 500, 374; 525/88, 92 R, 92 C, 89, 93, 98, 99

(56) References Cited

U.S. PATENT DOCUMENTS

| | | |
|---|---|---|
| 3,333,024 A | 7/1967 | Haelele et al. |
| 3,431,323 A | 3/1969 | Jones |
| 3,598,886 A | 8/1971 | Hoeg et al. |
| 3,644,588 A | 2/1972 | Hassell |
| 4,452,951 A | 6/1984 | Kubo et al. |
| 4,892,903 A | 1/1990 | Himes |
| 5,093,422 A | 3/1992 | Himes |
| 5,260,126 A | 11/1993 | Collier, IV et al. |
| 5,352,744 A | 10/1994 | Bates et al. |
| 5,612,422 A | 3/1997 | Hucul et al. |
| 5,654,253 A | 8/1997 | Hucul et al. |
| 5,700,878 A | 12/1997 | Hucul et al. |
| 5,905,097 A | 5/1999 | Walther |

FOREIGN PATENT DOCUMENTS

| | | |
|---|---|---|
| EP | 0 505 110 | 9/1992 |
| WO | WO 94/15997 | 7/1994 |
| WO | WO 94/21694 | 9/1994 |
| WO | 95/33006 | 12/1995 |
| WO | 96/34896 | 11/1996 |
| WO | 98/16582 | 4/1998 |
| WO | 00/77094 | 12/2000 |

OTHER PUBLICATIONS

SIR No. H1 808. Djiauw, et al., Extrudable Styrenic Block Copolymer Compositions Containing a Metallocene Polyolefin (Oct. 5, 1999).

Holden, Geoffrey et al., Thermoplastic Elastomers. pp. 301–305 (1996).

*Primary Examiner*—Jeffrey Mullis

(57) ABSTRACT

The present invention relates to a fiber produced form a composition comprising at least one hydrogenated block copolymer and, optionally, at least one other polymer selected from the group consisting of a reactive tailored liquid polyurethane, an elastomeric or sulfonated ethylene/vinyl aromatic interpolymer, an elastomeric ethylene/$C_3$–$C_{20}$ α-olefin interpolymer, an $C_3$–$C_{20}$ α-olefin/conjugated diene interpolymer, an elastic polypropylene polymer, an enhanced polypropylene polymer, an elastomeric thermoplastic polyurethane, an elastic copolyester, a partially hydrogenated block copolymer, an elastic polyamide, a hydroxyl functionalized polyether (or polyetheramine), a styrene/conjugated diene interpolymer, and an elastomeric metallocene-catalyzed synthetic polymer or a blend or formulated system thereof.

26 Claims, 7 Drawing Sheets

HYDROGENATED BLOCK COPOLYMERS HAVING ELASTICITY AND ARTICLES MADE THEREFROM

CROSS REFERENCE TO RELATED APPLICATIONS

This application is a CIP of U.S. Ser. No. 09/627,727 filed Jul. 28, 2000 now abandoned, which claims the benefit of U.S. Provisional Application No. 60/146,008, filed Jul. 28, 1999, now expired, U.S. Provisional Application No. 60/197,161, filed Apr. 13, 2000, now expired, and U.S. Provisional Application No. 60/203,558, filed May 11, 2000, now expired.

FIELD OF THE INVENTION

The present invention relates to an elastic fiber produced from a composition comprising at least one hydrogenated block copolymer. In particular, the invention pertains to elastic articles such as, for example, but not limited to, elastic fabric, as well as composites comprising the same, especially a composite absorbent item comprising at least one elastic article.

BACKGROUND OF THE INVENTION

Materials with excellent stretchability and elasticity are needed to manufacture a variety of disposal and durable articles such as, for example, incontinence pads, disposable diapers, training pants, sports apparel and furniture upholstery.

Disposable articles are typically elastic composite materials prepared from a combination of polymer film, fibers, sheets and absorbent materials as well as a combination of fabrication technologies. Whereas the fibers are prepared by well known processes such as spun bonding, melt blowing, melt spinning and continuous filament wounding techniques, the film and sheet forming processes typically involve known extrusion and coextrusion techniques, e.g., blown film, cast film, profile extrusion, injection molding, extrusion coating, and extrusion sheeting.

A material is typically characterized as elastic where it has a high percent elastic recovery (i.e., a low percent permanent set) after application of a biasing force. Ideally, elastic materials are characterized by a combination of three important properties, i.e., a low percent permanent set, a low stress or load at strain, and a low percent stress or load relaxation. That is, there should be (1) a low stress or load requirement to stretch the material, (2) no or low relaxing of the stress or unloading once the material is stretched, and (3) complete or high recovery to original dimensions after the stretching, biasing or straining is discontinued.

Lycra (a spandex supplied by Dupont Chemical Company) is a segmented polyurethane elastic material that is known to exhibit good elastic properties. But Lycra tends to be extremely cost prohibitive in several applications. Also, Lycra like natural rubbers tends to exhibit poor environmental resistance to ozone, chlorine and high temperature, especially in the presence of moisture.

Block polymers generally are elastomeric materials that exhibit excellent solid-state elastic performance attributes. But unsaturated block polymers such as, for example, styrene-butadiene-styrene triblock polymers, tend to exhibit mediocre thermal stability, especially in the molten state and poor UV stability.

Conversely, known partially hydrogenated (or partially saturated) styrene block copolymers (for example, KRATON G block copolymers supplied by Shell Chemical Company) are difficult to melt process and draw into fibers or films. In fact, preparation of fine denier fiber (that is, less than or equal to 40 denier) or thin film (that is, less than or equal to 2 mils) from partially hydrogenated or partially saturated block polymers is generally not possible at commercial fabrication rates. To overcome characteristic melt processing and drawing difficulties, partially hydrogenated block copolymers are commonly formulated with various additives such as oils, waxes and tackifiers. But in order to achieve good melt processability and drawability, very high levels of low molecular weight additives are typically required which tend to compromise strength and elastic properties.

WO 95/33006 discloses blends of styrene block polymers with substantially linear ethylene polymers. This disclosure describes as one advantage of blending with substantially linear ethylene polymers an improvement in processability. That is, the ethylene polymers are described as fusion promoters and processing aids which reduce the processing delay times characteristic of (partially) saturated styrene block copolymers.

Hydrogenated block copolymers of vinyl aromatic and conjugated dienes such as styrene-butadiene-styrene polymers are well known in the art. U.S. Pat. Nos. 3,333,024; 3,431,323; 3,598,886; 5,352,744; 3,644,588 (the disclosures of all of which are incorporated herein by reference) and EP-505,110, disclose various hydrogenated block copolymers. In particular, full hydrogenation of the aromatic ring of the block polymers has been investigated. But polymer scientists contend that fully hydrogenated styrene-butadiene-styrene copolymers (that is, complete saturation of the vinyl aromatic monomer unit as well as the conjugated diene monomer unit) have no useful properties at elevated temperatures, even if only slightly elevated. For example, Thermoplastic Elastomers, 2d edition, 1996, page 304, lines 8–12, states "Thus, polystyrene remains the choice for any amorphous hydrocarbon block copolymer. This last fact is clearly demonstrated in the case of the fully hydrogenated VCH-EB-VCH polymer. The interaction parameter is so severely reduced by hydrogenation that at only slightly elevated temperatures, the polymer loses all strength and appears to be homogeneously mixed at ordinary melt temperatures."

In spite of various disclosures relating to elastic materials, including disclosures pertaining to hydrogenated block copolymers as well as blends consisting of block polymers and ethylene polymers, such as for example U.S. Pat. No. 5,093,422 to Himes and SIR No. H1,808 to Djiauw et al., there is a present need for cost-effective elastic materials (and articles thereof) having good processability while maintaining strength and elastic properties.

SUMMARY OF THE INVENTION

We have discovered that a composition comprising at least one substantially hydrogenated block copolymer, surprisingly exhibits improved melt drawability and processability, (and in certain embodiments improved elastic properties) while providing retained or improved strength properties in fibers produced therefrom.

We have also discovered that this composition can be conveniently used to prepare improved disposable and durable elastic articles with or without the use of various additives such as processing aids, oils, waxes, polyolefins and tackifiers.

One aspect of the present invention is a fiber produced from a composition comprising at least one substantially hydrogenated block copolymer characterized as having i) a weight ratio of conjugated diene monomer unit to vinyl aromatic monomer unit before hydrogenation of greater than or equal to 60:40;

ii) a weight average molecular weight (Mw) before hydrogenation of from about 30,000 to about 150,000, wherein each vinyl aromatic monomer unit (A) has a weight average molecular weight, Mwa, of from about 5,000 to about 45,000 and each conjugated diene monomer unit (B) has a weight average molecular weight, Mwb, of from about 12,000 to about 110,000; and iii) a hydrogenation level such that each vinyl aromatic monomer unit block is hydrogenated to a level of greater than 90 percent and each conjugated diene monomer unit block is hydrogenated to a level of greater than 95 percent, as determined using UV-VIS spectrophotometry and proton NMR analysis.

In one preferred embodiment, the composition, or fiber or article therefrom, is irradiated or crosslinked using any suitable technique, including ultraviolet irradiation and silane curing. Preferably, however, irradiation or crosslinking is effectuated using ionizing radiation provided by electron beam irradiation. Preferably, the extrudate, filament, web or part is permitted to cool or is quenched to ambient temperature (i.e., permitted to substantially solidify) before the application of additional heating or ionizing radiation to effectuate irradiation or crosslinking. Most preferably, the electron beam radiation is conducted under an inert atmosphere such as, for example, under nitrogen. In another embodiment of the invention, the fiber may be produced from a composition additionally comprising at least one other polymeric material such as a homogeneously branched ethylene polymer, especially a substantially linear ethylene polymer.

Surprisingly, it as been discovered that substantially hydrogenated block copolymers, even at molecular weights substantially higher than comparative partially hydrogenated block copolymers, can be successfully melt drawn, including meltspun into fine denier fibers, where the comparative block polymer cannot be melt drawn nor meltspun into fibers at any denier. This discovery is believed to be attributable to the surprising low shear melt viscosities of substantially hydrogenated block copolymers. Ordinarily, polymeric materials with higher molecular weights are expected to exhibit commensurately higher melt viscosities (and subsequently, poor processability and melt drawability) and certainly are not expected to exhibit dramatically lower viscosities.

DETAILED DESCRIPTION OF THE INVENTION

Figure 1:
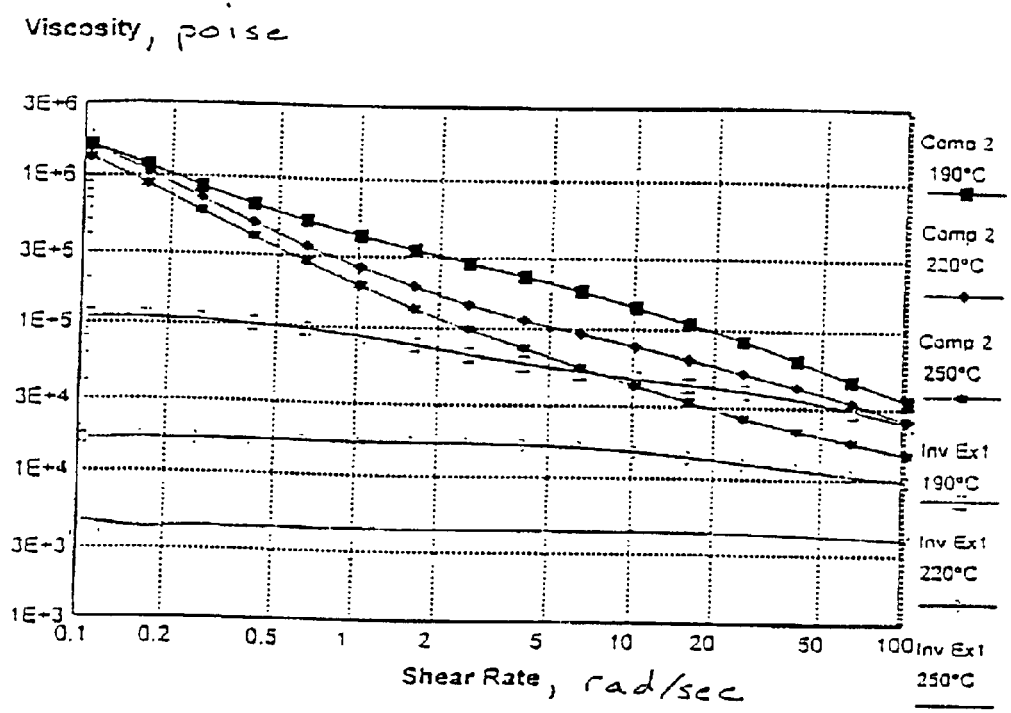
FIG. 1 is a plot of the low shear rheology of Inventive Example 1 and comparative run 2.

Substantially hydrogenated block copolymers comprise at least one distinct block of a hydrogenated polymerized vinyl aromatic monomer and at least one block of a hydrogenated polymerized conjugated diene monomer. Preferred substantially hydrogenated block copolymers are triblock comprising (before hydrogenation) two vinyl aromatic monomer unit blocks and one conjugated diene monomer unit block. Suitable substantially hydrogenated block copolymers for use in the present invention are generally characterized by:

a) a weight ratio of conjugated diene monomer unit block to vinyl aromatic monomer unit block before hydrogenation of greater than 60:40 b) a weight average molecular weight ($M_w$) before hydrogenation of from about 30,000 to about 150,000 (preferably, especially for high drawdown application such as, for example, fiber spinning, less than or equal to 81,000), wherein each vinyl aromatic monomer unit block (A) has a weight average molecular weight, $Mw_a$, of from about 5,000 to about 45,000 and each conjugated diene monomer unit block (B) has a weight average molecular weight, $Mw_b$, of from about 12,000 to about 110,000; and c) a hydrogenation level such that each vinyl aromatic monomer unit block is hydrogenated to a level of greater than 90 percent and each conjugated diene monomer unit block is hydrogenated to a level of greater than 95 percent, as determined using UV-VIS spectrophotometry and proton NMR analysis.

Neat substantially hydrogenated block copolymers can be further characterized as having a viscosity at 0.1 rad/sec and 190° C., as determined using a parallel plate rheometer (Rheometrics RMS-800 equipped with 25 mm diameter flat plates at 1.5 mm gap under a nitrogen purge), that is less than 1,000,000 poises, preferably less than or equal to 750,000 poises, more preferably less than 500,000 poises or that is at least 30 percent, preferably at least 50 percent, more preferably at least 80 lower than that of a partially hydrogenated block copolymer having the same monomer types, number of monomer units, symmetry and weight average molecular weight, or that is defined by the following inequality:

$$\text{Ln viscosity at } 0.1 \text{ rad/sec} \leq (7.08 \times 10^{-5})(M_w) + 7.89$$

where "Ln" means natural log and "≦" means less than or equal to.

Neat substantially hydrogenated block copolymers can also be further characterized as having a drawability of less than or equal to 200 denier, preferably less than or equal to 175 denier, more preferably less than or equal to 50 denier when fiber spun at 0.43 g/minute and 250° C. using an Instron capillary rheometer equipped with a die having a 1,000 micron diameter and a 20:1 $l/D$. The term "neat" is used herein to mean unblended with other synthetic polymer.

The vinyl aromatic monomer is typically a monomer of the formula:

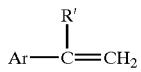

wherein R' is hydrogen or alkyl, Ar is phenyl, halophenyl, alkylphenyl, alkylhalophenyl, naphthyl, pyridinyl, or anthracenyl, wherein any alkyl group contains 1 to 6 carbon atoms which may be mono or multisubstituted with functional groups such as halo, nitro, amino, hydroxy, cyano, carbonyl and carboxyl. More preferably Ar is phenyl or alkyl phenyl with phenyl being most preferred. Typical vinyl aromatic monomers include styrene, alpha-methylstyrene, all isomers of vinyl toluene, especially para-vinyl toluene, all isomers of ethyl styrene, propyl styrene, butyl styrene, vinyl biphenyl, vinyl naphthalene, vinyl anthracene and mixtures thereof. The block copolymer can contain more than one specific polymerized vinyl aromatic monomer. In other words, the block copolymer can contain a polystyrene block and a poly-alpha-methylstyrene block. The hydrogenated vinyl aromatic block may also be a copolymer, wherein the hydrogenated vinyl aromatic portion is at least 50 weight percent of the copolymer.

The conjugated diene monomer can be any monomer having 2 conjugated double bonds. Such monomers include for example 1,3-butadiene, 2-methyl-1,3-butadiene, 2-methyl-1,3 pentadiene, isoprene and similar compounds, and mixtures thereof. The block copolymer can contain more than one specific polymerized conjugated diene monomer. In other words, the block copolymer can contain a polybutadiene block and a polyisoprene block.

The conjugated diene polymer block can comprise materials that remain amorphous after the hydrogenation process, or materials which are capable of crystallization after hydrogenation. Hydrogenated polyisoprene blocks remain amorphous, while hydrogenated polybutadiene blocks can be either amorphous or crystallizable depending upon their structure. Polybutadiene can contain either a 1,2 configuration, which hydrogenates to give the equivalent of a 1-butene repeat unit, or a 1,4-configuration, which hydrogenates to give the equivalent of an ethylene repeat unit. Polybutadiene blocks having at least approximately 40 weight percent 1,2-butadiene content, based on the weight of the polybutadiene block, provides substantially amorphous blocks with low glass transition temperatures upon hydrogenation. Polybutadiene blocks having less than approximately 40 weight percent 1,2-butadiene content, based on the weight of the polybutadiene block, provide crystalline blocks upon hydrogenation. Depending on the final application of the polymer it may be desirable to incorporate a crystalline block (to improve solvent resistance) or an amorphous, more compliant block. In some applications, the block copolymer can contain more than one conjugated diene polymer block, such as a polybutadiene block and a polyisoprene block. The conjugated diene polymer block may also be a copolymer of a conjugated diene, wherein the conjugated diene portion of the copolymer is at least 50 weight percent of the copolymer. The conjugated diene polymer block may also be a copolymer of more than one conjugated diene, such as a copolymer of butadiene and isoprene.

Other polymeric blocks may also be included in the substantially hydrogenated block copolymers used in the present invention.

A "block" is herein defined as a polymeric segment of a copolymer which exhibits microphase separation from a structurally or compositionally different polymeric segment of the copolymer. Microphase separation occurs due to the incompatibility of the polymeric segments within the block copolymer. The separation of block segments can be detected by the presence of distinct glass transition temperatures. Microphase separation and block copolymers are generally discussed in "Block Copolymers-Designer Soft Materials", *PHYSICS TODAY*, February, 1999, pages 32–38. Suitable substantially hydrogenated block copolymers typically have a weight ratio of conjugated diene monomer unit block to vinyl aromatic monomer unit block before hydrogenation of from about 60:40 to about 95:5, preferably from about 65:35 to about 90:10, more preferably from about 70:30 to about 85:15, based on the total weight of the conjugated diene monomer unit and vinyl aromatic monomer unit blocks.

The total weights of the vinyl aromatic monomer unit block(s) and the conjugated diene monomer unit block(s) before hydrogenation is typically at least 80 weight percent, preferably at least 90, and more preferably at least 95 weight percent of the total weight of the hydrogenated block copolymer. More specifically, the hydrogenated block copolymer typically contains from 1 to 99 weight percent of a hydrogenated vinyl aromatic polymer (e.g. polyvinylcyclohexane or PVCH block, generally from 10, preferably from 15, more preferably from 20, even more preferably from 25, and most preferably from 30 to 90 weight percent, preferably to 85 and most preferably to 80 percent, based on the total weight of the hydrogenated block copolymer. And, as to the conjugated diene polymer block, the hydrogenated block copolymer typically contains from 1 to 99 weight percent of a hydrogenated conjugated diene polymer block, preferably from 10, more preferably from 15, and most preferably from 20 to 90 weight percent, typically to 85, preferably to 80, more preferably to 75, even more preferably to 70 and most preferably to 65 percent, based on the total weight of the copolymer.

The substantially hydrogenated block copolymers suitable for use in the present invention are produced by the hydrogenation of block copolymers including triblock, multiblock, tapered block, and star block polymers such as, for example, but not limited to, SBS, SBSBS, SIS, SISIS, and SISBS (wherein S is polystyrene, B is polybutadiene and I is polyisoprene). Preferred block polymers contain at least one block segment comprised of a vinyl aromatic polymer block, more preferably the block polymer is symmetrical such as, for example, a triblock with a vinyl aromatic polymer block on each end. The block polymers may, however, contain any number of additional blocks, wherein these blocks may be attached at any point to the triblock polymer backbone. Thus, linear blocks would include, for example, SBS, SBSB, SBSBS, and SBSBSB. That is, suitable block polymers include asymmetrical block polymers and tapered linear block polymers.

The block polymer can also be branched, wherein polymer chains are attached at any point along the polymer backbone. In addition, blends of any of the aforementioned block copolymers can also be used as well as blends of the block copolymers with their hydrogenated homopolymer counterparts. In other words, a hydrogenated SBS block polymer can be blended with a hydrogenated SBSBS block polymer or a hydrogenated polystyrene homopolymer or both. It should be noted here that in the production of triblock polymers, small amounts of residual diblock copolymers are often produced.

The weight average molecular weight ($M_w$) of suitable substantially hydrogenated block copolymers, as measured before hydrogenation, is generally from 30,000, preferably from 45,000, more preferably from 55,000 and most preferably from 60,000 to 150,000, typically to 140,000, generally to 135,000, preferably to 130,000, more preferably to 125,000, and most preferably to 120,000. But preferably, especially when used neat for fiber melt spinning purposes, the weight average molecular weight before hydrogenation will be less than or equal to 81,500, more preferably less than or equal to 75,000 and most preferably less than or equal to 67,500.

Weight average molecular weight (Mw) and number average molecular weight (Mn) can both be used to describe the polymers listed herein. Because these polymers tend to have very narrow molecular weight polydispersities, the difference between Mn and Mw will be minimal. In fact, in some cases the number average molecular weight and the number average molecular weight will be the same. Therefore, Mn can also be read as Mw throughout this application.

Substantially hydrogenated block copolymers can have vinyl aromatic monomer unit block with weight average molecular weights, Mw, before hydrogenation of from about 6,000, especially from about 9,000, more especially from about 11,000, and most especially from about 12,000 to about 45,000, especially to about 35,000, more especially to about 25,000 and most especially to about 20,000. The weight average molecular weight of the conjugated diene monomer unit block before hydrogenation can be from about 12,000, especially from about 27,000, more especially from about 33,000 and most especially from about 36,000 to about 110,000, especially to about 100,000, more especially to about 90,000 and most especially to about 80,000. But preferably, especially when used neat for fiber melt spinning purposes, for triblocks comprising two hydrogenated vinyl aromatic monomer unit blocks and one hydrogenated conjugated diene monomer unit block, the weight average molecular weight of each vinyl aromatic monomer unit block before hydrogenation will be less than or equal to 15,000, typically less than 14,000, generally less than 13,500, advantageously less than 13,000, preferably less than 12,500, more preferably less than 12,000, even more preferably less than 11,500 and most preferably less than or equal to 11,000.

It is important to note that each individual block of the hydrogenated block copolymer of the present invention, can have its own distinct molecular weight. In other words, for example, two vinyl aromatic polymer blocks may each have a different molecular weight.

$M_p$ and $M_w$, as used to throughout the specification, are determined using gel permeation chromatography (GPC). The molecular weight of the substantially hydrogenated block copolymer and properties obtained are dependent upon the molecular weight of each of the monomer unit blocks. For substantially hydrogenated block copolymers, molecular weights are determined by comparison to narrow polydispersity homopolymer standards corresponding to the different monomer unit segments (for example, polystyrene and polybutadiene standards are used for SBS block copolymers) with adjustments based on the composition of the block copolymer. Also for example, for a triblock copolymer composed of styrene (S) and butadiene (B), the copolymer molecular weight can be obtained by the following equation:

$$\ln Mc = x \ln Ma + (1-x)\ln Mb$$

where Mc is the molecular weight of the copolymer, x is the weight fraction of S in the copolymer, Ma is the apparent molecular based on the calibration for S homopolymer and Mb is the apparent molecular weight based on the calibration for homopolymer B. This method is described in detail by L. H. Tung, *Journal of Applied Polymer Science*, volume 24,953,1979.

Methods of making block polymers are well known in the art. Typically, block polymers are made by anionic polymerization, examples of which are cited in *Anionic Polymerization: Principles and Practical Applications*, H. L. Hsieh and R. P. Quirk, Marcel Dekker, New York, Block polymers can be made by sequential monomer addition to a carbanionic initiator such as sec-butyl lithium or n-butyl lithium. Block polymers can also be made by coupling a triblock material with a divalent coupling agent such as 1,2-dibromoethane, dichlorodimethylsilane, or phenylbenzoate. In this method, a small chain (less than 10 monomer repeat units) of a conjugated diene monomer can be reacted with the vinyl aromatic monomer unit coupling end to facilitate the coupling reaction. Note, however, vinyl aromatic polymer blocks are typically difficult to couple, therefore, this technique is commonly used to achieve coupling of the vinyl aromatic polymer ends. The small chain of the conjugated diene monomer unit does not constitute a distinct block since no microphase separation is achieved.

Coupling reagents and strategies which have been demonstrated for a variety of anionic polymerizations are discussed in Hsieh and Quirk, Chapter 12, pgs. 307–331. In another method, a difunctional anionic initiator is used to initiate the polymerization from the center of the block system, wherein subsequent monomer additions add equally to both ends of the growing polymer chain. An example of a such a difunctional initiator is 1,3-bis(1-phenylethenyl) benzene treated with organolithium compounds, as described in U.S. Pat. Nos. 4,200,718 and 4,196,154, which are incorporated herein by reference.

After preparation of the block polymer, the polymer is hydrogenated to remove sites of unsaturation in both the conjugated diene monomer unit block(s) and the vinyl aromatic monomer unit block(s) of the polymer. Any method of hydrogenation can be used where suitable methods typically include the use of metal catalysts supported on an inorganic substrate, such as Pd on $BaSO_4$ (U.S. Pat. No. 5,352,744) and Ni on kieselguhr (U.S. Pat. No. 3,333,024), both of which are incorporated herein by reference. Additionally, soluble, homogeneous catalysts such those prepared from combinations of transition metal salts of 2-ethylhexanoic acid and alkyl lithiums can be used to fully saturate block copolymers, as described in *Die Makromolekulare Chemie*, Volume 160, pp. 291, 1972. Hydrogenation can also be achieved using hydrogen and a heterogeneous catalyst such as those described in U.S. Pat. Nos. 5,352,744; 5,612,422 and 5,645,253, the disclosures of which are incorporated herein by reference. The catalysts described therein are heterogeneous catalysts consisting of a metal crystallite supported on a porous silica substrate. An example of a silica supported catalyst which is especially useful in the polymer hydrogenation is a silica which has a surface area of at least 10 $m^2/g$ which is synthesized such that is contains pores with diameters ranging between 3000 and 6000 Angstroms. This silica is then impregnated with a metal capable of catalyzing hydrogenation of the polymer, such as nickel, cobalt, rhodium, ruthenium, palladium, platinum, other Group VIII metals, combinations or alloys thereof. Other heterogeneous catalysts can also be used, having average pore diameters in the range of 500 to 3,000 Angstroms.

The level of hydrogenation of the substantially hydrogenated block copolymers used in the present invention is greater than 95 percent for the conjugated diene monomer unit block(s) and greater than 90 percent for the vinyl aromatic monomer unit block(s), preferably greater than 99 percent for the conjugated diene monomer unit block(s) and greater than 95 percent for the vinyl aromatic monomer unit block(s), more preferably greater than 99.5 percent for the conjugated diene monomer unit block(s) and greater than 98 percent for the vinyl aromatic monomer unit block(s), and most preferably greater than 99.9 percent for the conjugated diene monomer unit block(s) and 99.5 percent for the vinyl aromatic monomer unit block(s).

The term "level of hydrogenation" refers to the percentage of the original unsaturated bonds that become saturated upon hydrogenation. The level of hydrogenation for the (hydrogenated) vinyl aromatic monomer unit block(s) can be determined using UV-VIS spectrophotometry, while the level of hydrogenation for the (hydrogenated) diene conjugated monomer unit block(s) can be determined using proton NMR.

The block polymer composition (i.e. ratio of conjugated diene monomer unit blocks to vinyl aromatic monomer unit blocks) can be determined using proton NMR and a comparative integration technique such as that described by Santee, Chang and Morton in *Journal of Polymer Science: Polymer Letter Edition*, Vol. 11, page 449 (1973). Conveniently, a Varian Inova NMR unit set at 300 MHz for $^1$H is used and samples of the block polymer are analyzed as 4 percent solutions (w/v) in $CDCl_3$ (deuterochloroform).

Individual block lengths can be calculated from the weight average molecular weight, $M_w$, and $^1$H NMR compositional analysis and by assuming a symmetrical structure (e.g. a triblock with terminal polystyrene blocks).

Polymer Blends and Mixtures

In addition to at least one substantially hydrogenated block copolymer, the composition used to produce the fibers of the present invention can optionally be made from a blend of a substantially hydrogenated block copolymer and another polymeric material. The term "blend" is used herein means a mixture or combination of at least one substantially hydrogenated block copolymer with at least one other polymeric material. The mixture or combination can be prepared by any known technique including melt blending, dry blending (e.g. tumble blending) or the solution mixing.

Suitable polymeric materials for blending with a substantially hydrogenated block copolymer include, but are not limited to, polyolefins, thermoplastic polyurethanes, polycarbonates, polyamides, polyethers, poly/vinyl chloride polymers, poly/vinylidene chloride polymers, polyesters, polymers that contain lactide acid residuals and partially or non-hydrogenated block copolymers.

Preferred polymeric materials for blending with a substantially hydrogenated block copolymer are other elastic polymers, such as, for example, but not limited to, a reactive tailored liquid polyurethane, an elastomeric or sulfonated ethylene/styrene interpolymer, an lastomeric ethylene/$C_3$–$C_{20}$ α-olefin interpolymer, an $C_3$–$C_{20}$ α-olefin/conjugated diene interpolymer, an elastic polypropylene polymer, an enhanced polypropylene polymer, an elastomeric thermoplastic polyurethane, an elastic copolyester (e.g. Hytrel™ from Dupont and Arnitel™ from Akzo), a partially hydrogenated block copolymer, an elastic polyamide, a styrene/conjugated diene interpolymer, and an elastomeric metallocene-catalyzed synthetic polymer.

But the most preferred blends are those comprised of a substantially hydrogenated block copolymer and a polyolefin elastomer or plastomer, especially a polyolefin elastomer or plastomer made using a single-site metallocene catalyst system (for example, a homogeneously branched ethylene polymer such as a substantially linear ethylene interpolymer or a homogeneously branched linear ethylene interpolymer). Blends of a substantially hydrogenated block copolymer and a polyolefin elastomer or plastomer have been discovered to exhibit unexpected synergistic processing/mechanical performance properties compared to either resins. In particular, blends of substantially hydrogenated block copolymer and a polyolefin elastomer or plastomer show surprisingly improved tenacity at break and elastic recovery at greater than 30 weight percent additions of substantially hydrogenated block copolymer.

Blends with a polypropylene polymer are also preferred, especially ternary blends that include a homogeneously branched ethylene polymer, for the preparation of fiber-containing fabrics that are processable at high stretching level as well as at high stretching rates. See, for example, U.S. provisional patent application Ser. No. 60/192,295, filed Mar. 27, 2000, in the names of Rexford Maugans et al., the disclosure of which is incorporated herein by reference, which describes polypropylene/ethylene polymer compositions that are referred to herein as "an enhanced polypropylene polymer".

Generally suitable polyolefins for blending include, for example, polyethylene (ethylene homopolymer), polystyrene, ethylene/alpha-olefin interpolymers, alpha-olefin homopolymers, such as polypropylene(propylene homopolymer), alpha-olefin interpolymers, such as interpolymers of polypropylene and an alpha-olefin having at least 4 carbon atoms.

Representative polyolefins include, for example, but are not limited to, substantially linear ethylene polymers, homogeneously branched linear ethylene polymers, heterogeneously branched linear ethylene (including linear low density polyethylene (LLDPE), ultra or very low density polyethylene (ULDPE or VLDPE) medium density polyethylene (MDPE) and high density polyethylene (HDPE)), high pressure low density polyethylene (LDPE), ethylene/acrylic acid (EAA) copolymers, ethylene/methacrylic acid (EMAA) copolymers, ethylene/acrylic acid (EAA) ionomers, ethylene/methacrylic acid (EMAA) ionomers, ethylene/vinyl acetate (EVA) copolymers, ethylene/vinyl alcohol (EVOH) copolymers, polypropylene homopolymers and copolymers, ethylene/propylene polymers, ethylene/styrene interpolymers, graft-modified polymers (e.g., maleic anhydride grafted polyethylene such as LLDPE g-MAH), ethylene acrylate copolymers (e.g. ethylene/ethyl acrylate (EEA) copolymers, ethylene/methyl acrylate (EMA), and ethylene/methmethyl acrylate (EMMA) copolymers), polybutylene (PB), ethylene carbon monoxide interpolymer (e.g., ethylene/carbon monoxide (ECO), copolymer, ethylene/acrylic acid/carbon monoxide (EAACO) terpolymer, ethylene/methacrylic acid/carbon monoxide (EMAACO) terpolymer, ethylene/vinyl acetate/carbon monoxide (EVACO) terpolymer and styrene/carbon monoxide (SCO)), chlorinated polyethylene and mixtures thereof.

As indicated above, ethylene/vinyl aromatic interpolymers may be used in the present invention. Preferred ethylene/vinyl aromatic interpolymers are substantially random ethylene/vinyl aromatic interpolymers, especially substantially random ethylene/styrene interpolymers. Representative of substantially random ethylene/vinyl aromatic interpolymers are substantially random ethylene/styrene interpolymers preferably containing at least 20, more preferably equal to or greater than 30, and most preferably equal to or greater than 50 weight percent interpolymerized styrene monomer.

A substantially random interpolymer comprises in polymerized form i) one or more α-olefin monomers and ii) one or more vinyl or vinylidene aromatic monomers and/or one or more sterically hindered aliphatic or cycloaliphatic vinyl or vinylidene monomers, and optionally iii) other polymerizable ethylenically unsaturated monomer(s).

The term "interpolymer" is used herein to indicate a polymer wherein at least two different monomers are polymerized to make the interpolymer.

The term "substantially random" in the substantially random interpolymer resulting from polymerizing i) one or more α-olefin monomers and ii) one or more vinyl or vinylidene aromatic monomers and/or one or more sterically hindered aliphatic or cycloaliphatic vinyl or vinylidene monomers, and optionally iii) other polymerizable ethylenically unsaturated monomer(s) as used herein generally means that the distribution of the monomers of said interpolymer can be described by the Bernoulli statistical model or by a first or second order Markovian statistical model, as described by J. C. Randall in *Polymer Sequence Determination, Carbon-13 NMR Method*, Academic Press New York, 1977, pp. 71–78. Preferably, the substantially random interpolymer resulting from polymerizing one or more α-olefin monomers and one or more vinyl or vinylidene aromatic monomers, and optionally other polymerizable ethylenically unsaturated monomer(s), does not contain more than 15 percent of the total amount of vinyl or vinylidene aromatic monomer in blocks of vinyl or vinylidene aromatic monomer of more than 3 units. More preferably, the interpolymer is not characterized by a high degree of either isotacticity or syndiotacticity. This means that in the carbon-13 NMR spectrum of the substantially random interpolymer, the peak areas corresponding to the main chain methylene and methine carbons representing either meso diad sequences or racemic diad sequences should not exceed 75 percent of the total peak area of the main chain methylene and methine carbons.

By the subsequently used term "substantially random interpolymer" it is meant a substantially random interpolymer produced from the above-mentioned monomers.

Suitable α-olefin monomers which are useful for preparing the substantially random interpolymer include, for example, α-olefin monomers containing from 2 to 20, preferably from 2 to 12, more preferably from 2 to 8 carbon atoms. Preferred such monomers include ethylene, propylene, butene-1,4-methyl-1-pentene, hexene-1 and octene-1. Most preferred are ethylene or a combination of ethylene with $C_3$–$C_8$ α-olefins. These α-olefins do not contain an aromatic moiety.

Suitable vinyl or vinylidene aromatic monomers which can be employed to prepare the substantially random interpolymer include, for example, those represented by the following formula I (formula 1)

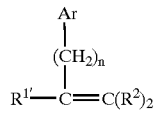

wherein $R^{1'}$ is selected from the group of radicals consisting of hydrogen and alkyl radicals containing from 1 to 4 carbon atoms, preferably hydrogen or methyl; each $R^2$ is independently selected from the group of radicals consisting of hydrogen and alkyl radicals containing from 1 to 4 carbon atoms, preferably hydrogen or methyl; Ar is a phenyl group or a phenyl group substituted with from 1 to 5 substituents; selected from the group consisting of halo, $C_1$–$C_4$-alkyl, and $C_1$–$C_4$-haloalkyl; and n has a value from zero to 4, preferably from zero to 2, most preferably zero. Particularly suitable such monomers include styrene and lower alkyl- or halogen-substituted derivatives thereof. Exemplary monovinyl or monovinylidene aromatic monomers include styrene, vinyl toluene, α-methylstyrene, t-butyl styrene or chlorostyrene, including all isomers of these compounds. Preferred monomers include styrene, α-methyl styrene, the lower alkyl-($C_1$–$C_4$) or phenyl-ring substituted derivatives of styrene, such as for example, ortho-, meta-, and para-methylstyrene, the ring halogenated styrenes, para-vinyl toluene or mixtures thereof. A more preferred aromatic monovinyl monomer is styrene.

By the term "sterically hindered aliphatic or cycloaliphatic vinyl or vinylidene monomers", it is meant addition polymerizable vinyl or vinylidene monomers corresponding to the formula:

wherein $A^1$ is a sterically bulky, aliphatic or cycloaliphatic substituent of up to 20 carbons, $R^{1'}$ is selected from the group of radicals consisting of hydrogen and alkyl radicals containing from 1 to 4 carbon atoms, preferably hydrogen or methyl; each $R^2$ is independently selected from the group of radicals consisting of hydrogen and alkyl radicals containing from 1 to 4 carbon atoms, preferably hydrogen or methyl; or alternatively $R^1$ and $A^1$ together form a ring system.

By the term "sterically bulky" is meant that the monomer bearing this substituent is normally incapable of addition polymerization by standard Ziegler-Natta polymerization catalysts at a rate comparable with ethylene polymerizations.

α-Olefin monomers containing from 2 to about 20 carbon atoms and having a linear aliphatic structure such as propylene, butene-1, hexene-1 and octene-1 are not considered as sterically hindered aliphatic monomers. Preferred sterically hindered aliphatic or cycloaliphatic vinyl or vinylidene compounds are monomers in which one of the carbon atoms bearing ethylenic unsaturation is tertiary or quaternary substituted. Examples of such substituents include cyclic aliphatic groups such as cyclohexyl, cyclohexenyl, cyclooctenyl, or ring alkyl or aryl substituted derivatives thereof, tert-butyl or norbornyl. Most preferred sterically hindered aliphatic or cycloaliphatic vinyl or vinylidene compounds are the various isomeric vinyl-ring substituted derivatives of cyclohexene and substituted cyclohexenes, and 5-ethylidene-2-norbornene. Especially suitable are 1-, 3-, and 4-vinylcyclohexene.

The substantially random interpolymers usually contain from about 0.5 to about 65, preferably from about 1 to about 55, more preferably from about 2 to about 50 mole percent of at least one vinyl or vinylidene aromatic monomer and/or sterically hindered aliphatic or cycloaliphatic vinyl or vinylidene monomer and from about 35 to about 99.5, preferably from about 45 to about 99, more preferably from about 50 to about 98 mole percent of at least one aliphatic α-olefin having from about 2 to about 20 carbon atoms.

Other optional polymerizable ethylenically unsaturated monomer(s) include strained ring olefins such as norbornene and $C_1$–$C_{10}$-alkyl or $C_6$–$C_{10}$-aryl substituted norbornenes, with an exemplary substantially random interpolymer being ethylene/styrene/norbornene.

The most preferred substantially random interpolymers are interpolymers of ethylene and styrene and interpolymers of ethylene, styrene and at least one α-olefin containing from 3 to 8 carbon atoms.

The number average molecular weight ($M_n$) of the substantially random interpolymers is usually greater than 5,000, preferably from about 20,000 to about 1,000,000, more preferably from about 50,000 to about 500,000. The glass transition temperature ($T_g$) of the substantially random interpolymers is preferably from about −40° C. to about +35° C., preferably from about 0° C. to about +30° C., most preferably from about +10° C. to about +25° C., measured according to differential mechanical scanning (DMS).

The substantially random interpolymers may be modified by typical grafting, hydrogenation, functionalizing, or other reactions well known to those skilled in the art. The polymers may be readily sulfonated or chlorinated to provide functionalized derivatives according to established techniques. The substantially random interpolymers may also be modified by various chain extending or crosslinking processes including, but not limited to peroxide-, silane-, sulfur-, radiation-, or azide-based cure systems. A full description of the various crosslinking technologies is described in copending U.S. patent application Ser. Nos. 08/921,641 and 08/921,642, both filed on Aug. 27, 1997, the entire contents of both of which are herein incorporated by reference.

Dual cure systems, which use a combination of heat, moisture cure, and radiation steps, may also be effectively employed. Dual cure systems are disclosed and claimed in U.S. patent application Ser. No. 536,022, filed on Sep. 29, 1995, in the names of K. L. Walton and S. V. Karande, incorporated herein by reference. For instance, it may be desirable to employ peroxide crosslinking agents in conjunction with silane crosslinking agents, peroxide crosslinking agents in conjunction with radiation, sulfur-containing crosslinking agents in conjunction with silane crosslinking agents, etc.

The substantially random interpolymers may also be modified by various crosslinking processes including, but not limited to the incorporation of a diene component as a termonomer in its preparation and subsequent crosslinking by the aforementioned methods and further methods including vulcanization via the vinyl group using sulfur for example as the cross linking agent.

One suitable method for manufacturing substantially random ethylene/vinyl aromatic interpolymers includes polymerizing a mixture of polymerizable monomers in the presence of one or more metallocene or constrained geometry catalysts in combination with various cocatalysts, as described in EP-A-0,416,815 by James C. Stevens et al. and U.S. Pat. No. 5,703,187 by Francis J. Timmers, both of which are incorporated herein by reference in their entirety. Preferred operating conditions for such polymerization reactions include pressures from atmospheric up to 3000 atmospheres and temperatures from −300° C. to 200° C. Polymerizations and unreacted monomer removal at temperatures above the auto-polymerization temperature of the respective monomers may result in formation of some amounts of homopolymer polymerization products resulting from free radical polymerization.

Examples of suitable catalysts and methods for preparing the substantially random interpolymers are disclosed in U.S. application Ser. No. 702,475, filed May 20, 1991 (EP-A-514,828); as well as U.S. Pat. Nos. 5,055,438; 5,057,475; 5,096,867; 5,064,802; 5,132,380; 5,189,192; 5,321,106; 5,347,024; 5,350,723; 5,374,696; 5,399,635; 5,470,993; 5,703,187; and 5,721,185, all of which patents and applications are incorporated herein by reference.

The substantially random ethylene/vinyl aromatic interpolymers can also be prepared by the methods described in JP 07/278230 employing compounds shown by the general formula

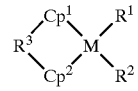

Where $Cp^1$ and $Cp^2$ are cyclopentadienyl groups, indenyl groups, fluorenyl groups, or substituents of these, independently of each other; $R^1$ and $R^2$ are hydrogen atoms, halogen atoms, hydrocarbon groups with carbon numbers of 1–12, alkoxyl groups, or aryloxyl groups, independently of each other; M is a group IV metal, preferably Zr or Hf, most preferably Zr; and $R^3$ is an alkylene group or silanediyl group used to crosslink $Cp^1$ and $Cp^2$.

The substantially random ethylene/vinyl aromatic interpolymers can also be prepared by the methods described by John G. Bradfute et al. (W. R. Grace & Co.) in WO 95/32095; by R. B. Pannell (Exxon Chemical Patents, inc.) in WO 94/00500; and in Plastics Technology p. 25 (September 1992).

Also suitable are the substantially random interpolymers which comprise at least one α-olefin/vinyl aromatic/vinyl aromatic/α-olefin tetrad disclosed in U.S. application Ser. No. 08/708,869, filed Sep. 4, 1996, and WO 98/09999, both by Francis J. Timmers et al., the disclosures of which are incorporated herein by reference. These interpolymers contain additional signals in their carbon-13 NMR spectra with intensities greater than three times the peak to peak noise. These signals appear in the chemical shift range 43.70–44.25 ppm and 38.0–38.5 ppm. Specifically, major peaks are observed at 44.1, 43.9, and 38.2 ppm. A proton test NMR experiment indicates that the signals in the chemical shift region 43.70–44.25 ppm are methine carbons and the signals in the region 38.0–38.5 ppm are methylene carbons.

It is believed that these new signals are due to sequences involving two head-to-tail vinyl aromatic monomer insertions preceded and followed by at least one α-olefin insertion, e.g. an ethylene/styrene/styrene/ethylene tetrad wherein the styrene monomer insertions of said tetrads occur exclusively in a 1,2 (head to tail) manner. It is understood by one skilled in the art that for such tetrads involving a vinyl aromatic monomer other than styrene and an α-olefin other than ethylene that the ethylene/vinyl aromatic monomer/vinyl aromatic monomer/ethylene tetrad will give rise to similar carbon-13 NMR peaks but with slightly different chemical shifts.

These interpolymers can be prepared by conducting the polymerization at temperatures of from about −30° C. to about 250° C. in the presence of such catalysts as those represented by the formula:

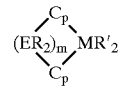

wherein each Cp is independently, each occurrence, a substituted cyclopentadienyl group n-bound to M; E is C or Si; M is a group IV metal, preferably Zr or Hf, most preferably Zr; each R is independently, each occurrence, H, hydrocarbyl, silahydrocarbyl, or hydrocarbylsilyl, containing up to 30, preferably from about 1 to about 20, more preferably from about 1 to about 10 carbon or silicon atoms; each R' is independently, each occurrence, H, halo, hydrocarbyl, hyrocarbyloxy, silahydrocarbyl, hydrocarbylsilyl containing up to 30, preferably from about 1 to about 20, more preferably from about 1 to about 10 carbon or silicon atoms or two R' groups together can be a $C_1$–$C_{10}$ hydrocarbyl substituted 1,3-butadiene; M is 1 or 2; and optionally, but preferably in the presence of an activating cocatalyst.

Particularly, suitable substituted cyclopentadienyl groups include those illustrated by the formula:

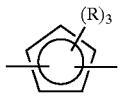

wherein each R is independently, each occurrence, H, hydrocarbyl, silahydrocarbyl, or hydrocarbylsilyl, containing up to 30, preferably from about 1 to about 20, more preferably from about 1 to about 10 carbon or silicon atoms or two R groups together form a divalent derivative of such group. Preferably, R independently each occurrence is (including where appropriate all isomers) hydrogen, methyl, ethyl, propyl, butyl, pentyl, hexyl, benzyl, phenyl or silyl or (where appropriate) two such R groups are linked together forming a fused ring system such as indenyl, fluorenyl, tetrahydroindenyl, tetrahydrofluorenyl, or octahydrofluorenyl.

Particularly preferred catalysts include, for example, racemic-(dimethylsilanediyl)-bis-(2-methyl-4-phenylindenyl) zirconium dichloride, racemic-(dimethylsilanediyl)-bis-(2-methyl-4-phenylindenyl) zirconium 1,4diphenyl-1,3-butadiene, racemic-(dimethylsilanediyl)-bis-(2-methyl-4-phenylindenyl) zirconium di-$C_1$–$C_4$ alkyl, racemic-(dimethylsilanediyl)-bis-(2-methyl-4-phenylindenyl) zirconium di-$C_1$–$C_4$ alkoxide, or any combination thereof and the like.

It is also possible to use the following titanium-based constrained geometry catalysts, [n-(1,1-dimethylethyl)-1,1-dimethyl-I-[(1,2,3,4,5-η)-1,5,6,7-tetrahydro-s-indacen-I-yl] silanaminato(2-)-n]titanium dimethyl; (1-indenyl)(tert-butylamido)dimethyl-silane titanium dimethyl; ((3-tert-butyl)(1,2,3,4,5-η)-I-indenyl)(tert-butylamido) dimethylsilane titanium dimethyl; and ((3-iso-propyl)(1,2,3,4,5-η)-I-indenyl)(tert-butyl amido)dimethylsilane titanium dimethyl, or any combination thereof and the like.

Further preparative methods for the interpolymers used in the present invention have been described in the literature. Longo and Grassi (*Makromol. Chem.* Volume 191, pages 2387 to 2396 [1990]) and D'Anniello et al. (*Journal of Applied Polymer Science*, Volume 58, pages 1701–1706 [1995])ce, reported the use of a catalytic system based on methylalumoxane (MAO) and cyclopentadienyl-titanium trichloride ($CpTiCl_3$) to prepare an ethylene-styrene copolymer. Xu and Lin (*Polymer Preprints Am. Chem. Soc., Div. Polym. Chem.*), Volume 35, pages 686,687 [1994]), have reported copolymerization using a $MgCl_2/TiCl_4/NdCl_3/Al$ $(iBu)_3$ catalyst to give random copolymers of styrene and propylene. Lu et al (*Journal of Applied Polymer Science*, Volume 53, pages 1453 to 1460 [1994]), have described the copolymerization of ethylene and styrene using a $TiCl_4/NdCl_3/MgCl_2/al(Et)_3$ catalyst. Sernetz and Mulhaupt, (*Macromol. Chem. Phys.*, V. 197, pp. 1071–1083, 1997), have described the influence of polymerization conditions on the copolymerization of styrene with ethylene using $Me_2Si(Me_4 Cp)(n$-tert-butyl$)TiCl_2$/Methylaluminoxane Ziegler-Natta catalysts. Copolymers of ethylene and styrene produced by bridged metallocene catalysts have been described by Arai, Toshiaki and Suzuki (*Polymer Preprints Am. Chem. Soc., Div. Polym. Chem.*), Volume 38, pages 349, 350 [1997]) and in U.S. Pat. No. 5,652,315, issued to Mitsui Toatsu Chemicals, Inc., the disclosures of which are incorporated herein by reference.

Also, the manufacture of α-olefin/vinyl aromatic monomer interpolymers such as propylene/styrene and butene/styrene are described in U.S. Pat. No. 5,244,996, issued to Mitsui Petrochemical Industries Ltd. or U.S. Pat. No. 5,652,315 also issued to Mitsui Petrochemical Industries Ltd. or as disclosed in DE 197 11339 A1 to Denki Kagaku Kogyo KK. All of the above disclosures of methods for preparing the interpolymer component are incorporated herein by reference. Moreover, although of high isotacticity and therefore not "substantially random", the random copolymers of ethylene and styrene as disclosed in *Polymer Preprints*, Vol. 39, no. 1, March 1998 by Toru Aria et al. can also be employed as the ethylene polymer of the present invention.

While preparing the substantially random interpolymer, an amount of atactic vinyl aromatic homopolymer may be formed due to homopolymerization of the vinyl aromatic monomer at elevated temperatures. The presence of vinyl aromatic homopolymer is in general not detrimental for the purposes of the present invention and can be tolerated. The vinyl aromatic homopolymer may be separated from the interpolymer, if desired, by extraction techniques such as selective precipitation from solution with a non-solvent for either the interpolymer or the vinyl aromatic homopolymer. Nevertheless, for the purpose of the present invention, it is preferred that no more than 30 weight percent, preferably less than 20 weight percent (based on the total weight of the interpolymers) of atactic vinyl aromatic homopolymer be is present.

Suitable sulfonated ethylene/styrene interpolymers for use in the present invention are described in WO 99/20691.

Suitable reactive tailored liquid polyurethanes for use in the present invention are described in WO 99/16806.

Suitable hydroxyl functionalized polyethers and hydroxyl functionalized polyetheramines for use in the present invention are known in the art. See, for example, U.S. Pat. No. 5,275,853 and WO 00/1750, the disclosures of which are incorporated herein by reference.

The preferred polymeric material for blending with a substantially hydrogenated block copolymer is a polyolefin elastomer or plastomer characterized as having a DSC crystallinity of less than 45 weight percent, preferably less than 30 weight percent, more preferably less than or equal to 20 weight percent, and most preferably less than or equal 16 percent.

Preferably, the polyolefin elastomer or plastomer is characterized as having a melt index ($I_2$) less than 5,000 g/10 minutes, more preferably less than 500 g/10 minutes, most preferably less than or equal to 50 g/10 minutes, as determined in accordance with ASTM D-1238, Condition 190° C./2.16 kilogram (kg).

Also, preferably the polymeric material used for blending with the substantially hydrogenated block copolymer is characterized as having a percent permanent set of less than 75 at 23° C., preferably less than or equal 60 at 23° C., more preferably less than or equal to 30 at 23° C. and most preferably less than or equal to 15 at 23° C. and 38° C. and 200 percent strain when measured at a 2 mil thickness using an Instron tensiometer; or preferably a percent set elongation of less than or equal to 25, more preferably 20, most preferably 15 at 23° C. and 100 percent strain.

The term "polymer", as used herein, refers to a polymeric compound prepared by polymerizing monomers, whether of the same or a different type. As used herein, generic term "polymer" embraces the terms "homopolymer," "copolymer," "terpolymer" as well as "interpolymer."

The term "interpolymer", as used herein refers to polymers prepared by the polymerization of at least two different types of monomers. As used herein the generic term "interpolymer" includes the term "copolymers" (which is usually employed to refer to polymers prepared from two different monomers) as well as the term "terpolymers" (which is usually employed to refer to polymers prepared from three different types of monomers).

The term "homogeneously branched ethylene polymer" is used herein in the conventional sense to refer to an ethylene interpolymer in which the comonomer is randomly distributed within a given polymer molecule and wherein substantially all of the polymer molecules have the same ethylene to comonomer molar ratio. The term refers to an ethylene interpolymer that are manufactured using so-called homogeneous or single-site catalyst systems known in the art such Ziegler vanadium, hafnium and zirconium catalyst systems and metallocene catalyst systems e.g., a constrained geometry catalyst systems which is further described herein below.

Homogeneously branched ethylene polymers for use in the present invention can be also described as having less than 15 weight percent, preferably less 10 weight percent, more preferably less than 5 and most preferably zero (0) weight percent of the polymer with a degree of short chain branching less than or equal to 10 methyls/1000 carbons. That is, the polymer contains no measurable high density polymer fraction (e.g., there is no fraction having a density of equal to or greater than 0.94 g/cm$^3$), as determined, for example, using a temperature rising elution fractionation (TREF) technique and infrared or 13C nuclear magnetic resonance (NMR) analysis.

Preferably, the homogeneously branched ethylene polymer is characterized as having a narrow, essentially single melting TREF profile/curve and essentially lacking a measurable high density polymer portion, as determined using a temperature rising elution fractionation technique (abbreviated herein as "TREF").

The composition distribution of an ethylene interpolymer can be readily determined from TREF as described, for example, by Wild et al., *Journal of Polymer Science, Poly. Phys. Ed.*, Vol. 20, p. 441 (1982), or in U.S. Pat. Nos. 4,798,081; 5,008,204; or by L. D. Cady, "The Role of Comonomer Type and Distribution in LLDPE Product Performance," SPE Regional Technical Conference, Quaker Square Hilton, Akron, Ohio, October 1–2, pp. 107–119 (1985).

The composition (monomer) distribution of the interpolymer can also be determined using $^{13}$C NMR analysis in accordance with techniques described in U.S. Pat. Nos. 5,292,845; 4,798,081; 5,089,321 and by J. C. Randall, *Rev. Macromol. Chem. Phys.*, C29, pp. 201–317 (1989), the disclosures of all of which are incorporated herein by reference.

In analytical temperature rising elution fractionation analysis (as described in U.S. Pat. No. 4,798,081 and abbreviated herein as "ATREF"), the film or composition to be analyzed is dissolved in a suitable hot solvent (e.g., trichlorobenzene) and allowed to crystallized in a column containing an inert support (stainless steel shot) by slowly reducing the temperature. The column is equipped with both a refractive index detector and a differential viscometer (DV) detector. An ATREF-DV chromatogram curve is then generated by eluting the crystallized polymer sample from the column by slowly increasing the temperature of the eluting solvent (trichlorobenzene). The ATREF curve is also frequently called the short chain branching distribution (SCBD) or composition distribution (CD) curve, since it indicates how evenly the comonomer (e.g., octene) is distributed throughout the sample in that as elution temperature decreases, comonomer content increases. The refractive index detector provides the short chain distribution information and the differential viscometer detector provides an estimate of the viscosity average molecular weight. The composition distribution and other compositional information can also be determined using crystallization analysis fractionation such as the CRYSTAF fractionalysis package available commercially from PolymerChar, Valencia, Spain.

Preferred homogeneously branched ethylene polymers (such as, but not limited to, substantially linear ethylene polymers) have a single melting peak between –30 and 150° C., as determined using differential scanning calorimetry (DSC), as opposed to traditional Ziegler polymerized heterogeneously branched ethylene polymers (e.g., LLDPE and ULDPE or VLDPE) which have two or more melting points.

The single melting peak is determined using a differential scanning calorimeter standardized with indium and deionized water. The method involves about 5–7 mg sample sizes, a "first heat" to about 180° C. which is held for 4 minutes, a cool down at 10° C./min. to –30° C. which is held for 3 minutes, and heat up at 10° C./min. to 150° C. to provide a "second heat" heat flow vs. temperature curve from which the melting peak(s) is obtained. Total heat of fusion of the polymer is calculated from the area under the curve.

The homogeneously branched ethylene polymers for use in the invention can be either a substantially linear ethylene polymer or a homogeneously branched linear ethylene polymer.

The term "linear" as used herein means that the ethylene polymer does not have long chain branching. That is, the polymer chains comprising the bulk linear ethylene polymer have an absence of long chain branching, as in the case of traditional linear low density polyethylene polymers or linear high density polyethylene polymers made using Ziegler polymerization processes (e.g., U.S. Pat. No. 4,076,698 (Anderson et al.)), sometimes called heterogeneous polymers. The term "linear" does not refer to bulk high pressure branched polyethylene, ethylene/vinyl acetate copolymers, or ethylene/vinyl alcohol copolymers which are known to those skilled in the art to have numerous long chain branches.

The term "homogeneously branched linear ethylene polymer" refers to polymers having a narrow short chain branching distribution and an absence of long chain branching. Such "linear" uniformly branched or homogeneous polymers include those made as described in U.S. Pat. No. 3,645,992 (Elston) and those made using so-called single site catalysts in a batch reactor having relatively high ethylene concentrations (as described in U.S. Pat. No. 5,026,798 (Canich) or in U.S. Pat. No. 5,055,438 (Canich) or those made using constrained geometry catalysts in a batch reactor also having relatively high olefin concentrations (as described in U.S. Pat. No. 5,064,802 (Stevens et al.) or in EP 0 416 815 A2 (Stevens et al.)).

Typically, homogeneously branched linear ethylene polymers are ethylene/α-olefin interpolymers, wherein the α-olefin is at least one $C_3$–$C_{20}$ α-olefin (e.g., propylene, 1-butene, 1-pentene, 4-methyl-1-pentene, 1-hexene, 1-octene and the like) and preferably the at least one $C_3$–$C_{20}$ α-olefin is 1-butene, 1-hexene or 1-octene. Most preferably, the ethylene/α-olefin interpolymer is a copolymer of ethylene and a $C_3$–$C_{20}$ α-olefin, and especially an ethylene/$C_4$–$C_8$ α-olefin copolymer such as an ethylene/1-octene copolymer, ethylene/1-butene copolymer, ethylene/1-pentene copolymer or ethylene/1-hexene copolymer.

Suitable homogeneously branched linear ethylene polymers for use in the invention are sold under the designation of TAFMER™ by Mitsui Chemical Corporation and under the designations of EXACT™ and EXCEED™ resins by Exxon Chemical Company.

The term "substantially linear ethylene polymer" as used herein means that the bulk ethylene polymer is substituted, on average, with about 0.01 long chain branches/1000 total carbons to about 3 long chain branches/1000 total carbons (wherein "total carbons" includes both backbone and branch carbons). Preferred polymers are substituted with about 0.01 long chain branches/1000 total carbons to about 1 long chain branches/1000 total carbons, more preferably from about 0.05 long chain branches/1000 total carbons to about 1 long chain branched/1000 total carbons, and especially from about 0.3 long chain branches/1000 total carbons to about 1 long chain branches/1000 total carbons.

As used herein, the term "backbone" refers to a discrete molecule, and the term "polymer" or "bulk polymer" refers, in the conventional sense, to the polymer as formed in a reactor. For the polymer to be a "substantially linear ethylene polymer", the polymer must have at least enough molecules with long chain branching such that the average long chain branching in the bulk polymer is at least an average of from about 0.01/1000 total carbons to about 3 long chain branches/1000 total carbons.

The term "bulk polymer" as used herein means the polymer which results from the polymerization process as a mixture of polymer molecules and, for substantially linear ethylene polymers, includes molecules having an absence of long chain branching as well as molecules having long chain branching. Thus a "bulk polymer" includes all molecules formed during polymerization. It is understood that, for the substantially linear polymers, not all molecules have long chain branching, but a sufficient amount do such that the average long chain branching content of the bulk polymer positively affects the melt rheology (i.e., the shear viscosity and melt fracture properties) as described herein below and elsewhere in the literature.

Long chain branching (LCB) is defined herein as a chain length of at least one (1) carbon less than the number of carbons in the comonomer, whereas short chain branching (SCB) is defined herein as a chain length of the same number of carbons in the residue of the comonomer after it is incorporated into the polymer molecule backbone. For example, a substantially linear ethylene/1-octene polymer has backbones with long chain branches of at least seven (7) carbons in length, but it also has short chain branches of only six (6) carbons in length.

Long chain branching can be distinguished from short chain branching by using $^{13}C$ nuclear magnetic resonance (NMR) spectroscopy and to a limited extent, e.g. for ethylene homopolymers, it can be quantified using the method of Randall, (Rev. Macromol.Chem. Phys., C29 (2&3), p. 285–297 (1989)). However as a practical matter, current $^{13}C$ nuclear magnetic resonance spectroscopy cannot determine the length of a long chain branch in excess of about six (6) carbon atoms and as such, this analytical technique cannot distinguish between a seven (7) carbon branch and a seventy (70) carbon branch. The long chain branch can be as long as about the same length as the length of the polymer backbone.

Although conventional $^{13}C$ nuclear magnetic resonance spectroscopy cannot determine the length of a long chain branch in excess of six carbon atoms, there are other known techniques useful for quantifying or determining the presence of long chain branches in ethylene polymers, including ethylene/1-octene interpolymers. For example, U.S. Pat. No. 4,500,648, incorporated herein by reference, teaches that long chain branching frequency (LCB) can be represented by the equation $LCB=b/M_w$ wherein b is the weight average number of long chain branches per molecule and $M_w$ is the weight average molecular weight. The molecular weight averages and the long chain branching characteristics are determined by gel permeation chromatography and intrinsic viscosity methods, respectively.

Two other useful methods for quantifying or determining the presence of long chain branches in ethylene polymers, including ethylene/1-octene interpolymers are gel permeation chromatography coupled with a low angle laser light scattering detector (GPC-LALLS) and gel permeation chromatography coupled with a differential viscometer detector (GPC-DV). The use of these techniques for long chain branch detection and the underlying theories have been well documented in the literature. See, e.g., Zimm, G. H. and Stockmayer, W. H., J. Chem. Phys., 17, 1301 (1949) and Rudin, A., Modern Methods of Polymer Characterization, John Wiley & Sons, New York (1991) pp. 103–112, the disclosures of both of which are incorporated by reference.

A. Willem deGroot and P. Steve Chum, both of The Dow Chemical Company, at the Oct. 4, 1994 conference of the Federation of Analytical Chemistry and Spectroscopy Society (FACSS) in St. Louis, Mo., presented data demonstrating that GPC-DV is indeed a useful technique for quantifying the presence of long chain branches in substantially linear ethylene polymers. In particular, deGroot and Chum found that the level of long chain branches in substantially linear ethylene homopolymer samples measured using the Zimm-Stockmayer equation correlated well with the level of long chain branches measured using $^{13}C$ NMR.

Further, deGroot and Chum found that the presence of octene does not change the hydrodynamic volume of the polyethylene samples in solution and, as such, one can account for the molecular weight increase attributable to octene short chain branches by knowing the mole percent octene in the sample. By deconvoluting the contribution to molecular weight increase attributable to 1-octene short chain branches, deGroot and Chum showed that GPC-DV may be used to quantify the level of long chain branches in substantially linear ethylene/octene copolymers.

DeGroot and Chum also showed that a plot of $Log(I_2,$ melt index) as a function of Log(GPC Weight Average Molecular Weight) as determined by GPC-DV illustrates that the long chain branching aspects (but not the extent of long branching) of substantially linear ethylene polymers are comparable to that of high pressure, highly branched low density polyethylene (LDPE) and are clearly distinct from ethylene polymers produced using Ziegler-type catalysts such as titanium complexes and ordinary homogeneous catalysts such as hafnium and vanadium complexes.

For substantially linear ethylene polymers, the empirical effect of the presence of long chain branching is manifested as enhanced rheological properties which are quantified and expressed in terms of gas extrusion rheometry (GER) results and/or melt flow, $I_{10}/I_2$, increases.

The substantially linear ethylene polymers used in the present invention are a unique class of compounds that are further defined in U.S. Pat. No. 5,272,236, application Ser. No. 07/776,130, filed Oct. 15, 1991; U.S. Pat. No. 5,278,272, application Ser. No. 07/939,281, filed Sep. 2, 1992; and U.S. Pat. No. 5,665,800, application Ser. No. 08/730,766, filed Oct. 16, 1996, each of which is incorporated herein by reference.

Substantially linear ethylene polymers differ significantly from the class of polymers conventionally known as homogeneously branched linear ethylene polymers described above and, for example, by Elston in U.S. Pat. No. 3,645,992. As an important distinction, substantially linear ethylene polymers do not have a linear polymer backbone in the conventional sense of the term "linear" as is the case for homogeneously branched linear ethylene polymers.

Substantially linear ethylene polymers also differ significantly from the class of polymers known conventionally as heterogeneously branched traditional Ziegler polymerized linear ethylene interpolymers (for example, ultra low density polyethylene, linear low density polyethylene or high density polyethylene made, for example, using the technique disclosed by Anderson et al. in U.S. Pat. No. 4,076,698) in that substantially linear ethylene interpolymers are homogeneously branched polymers. Further, substantially linear ethylene polymers also differ from the class of heterogeneously branched ethylene polymers in that substantially linear ethylene polymers are characterized as essentially lacking a measurable high density or crystalline polymer fraction as determined using a temperature rising elution fractionation technique.

The substantially linear ethylene elastomers and plastomers for use in the present invention is characterized as having (a) melt flow ratio, $I_{10}/I_2 \geq 5.63$, (b) a molecular weight distribution, $M_w/M_n$, as determined by gel permeation chromatography and defined by the equation:

$$(M_w/M_n) \leq (I_{10}/I_2) - 4.63,$$

(c) a gas extrusion rheology such that the critical shear rate at onset of surface melt fracture for the substantially linear ethylene polymer is at least 50 percent greater than the critical shear rate at the onset of surface melt fracture for a linear ethylene polymer, wherein the substantially linear ethylene polymer and the linear ethylene polymer comprise the same comonomer or comonomers, the linear ethylene polymer has an $I_2$ and $M_w/M_n$ within ten percent of the substantially linear ethylene polymer and wherein the respective critical shear rates of the substantially linear ethylene polymer and the linear ethylene polymer are measured at the same melt temperature using a gas extrusion rheometer, (d) a single differential scanning calorimetry, DSC, melting peak between −30° and 150° C., and (e) a density less than or equal to 0.865 g/cm$^3$.

Determination of the critical shear rate and critical shear stress in regards to melt fracture as well as other rheology properties such as "rheological processing index" (PI), is performed using a gas extrusion rheometer (GER). The gas extrusion rheometer is described by M. Shida, R. N. Shroff and L. V. Cancio in *Polymer Engineering Science*, Vol. 17, No. 11, p. 770 (1977) and in *Rheometers for Molten Plastics* by John Dealy, published by Van Nostrand Reinhold Co. (1982) on pp. 97–99.

The processing index (PI) is measured at a temperature of 190° C., at nitrogen pressure of 2500 psig (17.2 MPa) using a 0.0296 inch (752 micrometers) diameter (preferably a 0.0143 inch (0.04 cm) diameter die for high flow polymers, e.g. 50–100 $I_2$ melt index or greater), 20:1 L/D die having an entrance angle of 180°. The GER processing index is calculated in millipoise units from the following equation:

$$PI = 2.15 \times 10^6 \, dyne/cm^2/(1000 \times shear\ rate),$$

where: $2.15 \times 10^6$ dyne/cm$^2$ is the shear stress at 2500 psi (17.2 MPa), and the shear rate is the shear rate at the wall as represented by the following equation:

$$32 \, Q'/(60 \, sec/min)(0.745)(Diameter \times 2.54 \, cm/in)^3,$$

where:

Q' is the extrusion rate (gms/min), 0.745 is the melt density of polyethylene (gm/cm$^3$), and Diameter is the orifice diameter of the capillary (inches).

The PI is the apparent viscosity of a material measured at apparent shear stress of $2.15 \times 10^6$ dyne/cm$^2$.

For substantially linear ethylene polymers, the PI is less than or equal to 70 percent of that of a conventional linear ethylene polymer having an $I_2$, $M_w/M_n$ and density each within ten percent of the substantially linear ethylene polymer.

An apparent shear stress vs. apparent shear rate plot is used to identify the melt fracture phenomena over a range of nitrogen pressures from 5250 (36.2 MPa) to 500 (3.4 MPa) psig using the die or GER test apparatus previously described. According to Ramamurthy in *Journal of Rheology*, 30(2), 337–357, 1986, above a certain critical flow rate, the observed extrudate irregularities may be broadly classified into two main types: surface melt fracture and gross melt fracture.

Surface melt fracture occurs under apparently steady flow conditions and ranges in detail from loss of specular gloss to the more severe form of "sharkskin". In this disclosure, the onset of surface melt fracture is characterized at the beginning of losing extrudate gloss at which the surface roughness of extrudate can only be detected by 40× magnification. The critical shear rate at onset of surface melt fracture for the substantially linear ethylene polymers is at least 50 percent greater than the critical shear rate at the onset of surface melt fracture of a linear ethylene polymer having about the same $I_2$ and $M_w/M_n$. Preferably, the critical shear stress at onset of surface melt fracture for the substantially linear ethylene polymers of the invention is greater than about $2.8 \times 10^6$ dyne/cm$^2$.

Gross melt fracture occurs at unsteady flow conditions and ranges in detail from regular (alternating rough and smooth, helical, etc.) to random distortions. For commercial acceptability, (e.g., in blown film products), surface defects should be minimal, if not absent. The critical shear rate at onset of surface melt fracture (OSMF) and critical shear stress at onset of gross melt fracture (OGMF) will be used herein based on the changes of surface roughness and configurations of the extrudates extruded by a GER. For the substantially linear ethylene polymers used in the invention, the critical shear stress at onset of gross melt fracture is preferably greater than about $4 \times 10^6$ dyne/cm$^2$.

For the processing index determination and for the GER melt fracture determination, substantially linear ethylene polymers are tested without inorganic fillers and do not have more than 20 ppm (parts per million) aluminum catalyst residue. Preferably, however, for the processing index and melt fracture tests, substantially linear ethylene polymers do contain antioxidants such as phenols, hindered phenols, phosphites or phosphonites, preferably a combination of a phenol or hindered phenol and a phosphite or a phosphonite.

The molecular weights and molecular weight distributions are determined by gel permeation chromatography (GPC). A suitable unit is a Waters 150C high temperature chromatographic unit equipped with a differential refractometer and three columns of mixed porosity where columns are supplied by Polymer Laboratories and are commonly packed with pore sizes of $10^3$, $10^4$, $10^5$ and $10^6$ Å. For ethylene polymers, the unit operating temperature is about 140° C. and the solvent is 1,2,4-trichlorobenzene, from which about 0.3 percent by weight solutions of the samples are prepared for injection. Conversely, for the substantially hydrogenated block copolymers, the unit operating temperature is about 25° C. and tetrahydrofuran is used as the solvent. A suitable flow rate is about 1.0 milliliters/minute and the injection size is typically about 100 microliters.

For the ethylene polymers where used in the present invention, the molecular weight determination with respect to the polymer backbone is deduced by using narrow molecular weight distribution polystyrene standards (from Polymer Laboratories) in conjunction with their elution volumes. The equivalent polyethylene molecular weights are determined by using appropriate Mark-Houwink coefficients for polyethylene and polystyrene (as described by Williams and Ward in *Journal of Polymer Science*, Polymer Letters, Vol. 6, p. 621, 1968 to derive the following equation:

$$M_{polyethylene}=a*(M_{polystyrene})^b.$$

In this equation, a=0.4316 and b=1.0. Weight average molecular weight, $M_w$, is calculated in the usual manner according to the following formula: $M_j=(\Sigma w_i(M_i^j))^j$. Where $w_i$ is the weight fraction of the molecules with molecular weight $M_i$ eluting from the GPC column in fraction i and j=1 when calculating $M_w$ and j=−1 when calculating $M_n$.

For the at least one homogeneously branched ethylene polymer used in the present invention, the $M_w/M_n$ is preferably less than 3.5, more preferably less than 3.0, most preferably less than 2.5, and especially in the range of from about 1.5 to about 2.5 and most especially in the range from about 1.8 to about 2.3.

Substantially linear ethylene polymers are known to have excellent processability, despite having a relatively narrow molecular weight distribution (that is, the $M_w/M_n$ ratio is typically less than about 3.5). Surprisingly, unlike homogeneously and heterogeneously branched linear ethylene polymers, the melt flow ratio ($I_{10}/I_2$) of substantially linear ethylene polymers can be varied essentially independently of the molecular weight distribution, $M_w/M_n$. Accordingly, especially when good extrusion processability is desired, the preferred ethylene polymer for use in the present invention is a homogeneously branched substantially linear ethylene interpolymer.

Suitable constrained geometry catalysts for use manufacturing substantially linear ethylene polymers include constrained geometry catalysts as disclosed in U.S. application Ser. No. 07/545,403, filed Jul. 3, 1990; U.S. application Ser. No. 07/758,654, filed Sep. 12, 1991; U.S. Pat. No. 5,132,380 (application Ser. No. 07/758,654); U.S. Pat. No. 5,064,802 (application Ser. No. 07/547,728); U.S. Pat. No. 5,470,993 (application Ser. No. 08/241,523); U.S. Pat. No. 5,453,410 (application Ser. No. 08/108,693); U.S. Pat. No. 5,374,696 (application Ser. No. 08/08,003); U.S. Pat. No. 5,532,394 (application Ser. No. 08/295,768); U.S. Pat. No. 5,494,874 (application Ser. No. 08/294,469); and U.S. Pat. No. 5,189,192 (application Ser. No. 07/647,111), the teachings of all of which are incorporated herein by reference.

Suitable catalyst complexes may also be prepared according to the teachings of WO 93/08199. Further, the monocyclopentadienyl transition metal olefin polymerization catalysts taught in U.S. Pat. No. 5,026,798, which is incorporated herein by reference, are also believed to be suitable for use in preparing the polymers of the present invention, so long as the polymerization conditions substantially conform to those described in U.S. Pat. Nos. 5,272,236; 5,278,272 and 5,665,800, especially with strict attention to the requirement of continuous polymerization. Such polymerization methods are also described in PCT/US 92/08812 (filed Oct. 15, 1992).

The foregoing catalysts may be further described as comprising a metal coordination complex comprising a metal of groups 3–10 or the Lanthanide series of the Periodic Table of the Elements and a delocalize β-bonded moiety substituted with a constrain-inducing moiety, said complex having a constrained geometry about the metal atom such that the angle at the metal between the centroid of the delocalized, substituted pi-bonded moiety and the center of at least one remaining substituent is less than such angle in a similar complex containing a similar pi-bonded moiety lacking in such constrain-inducing substituent, and provided further that for such complexes comprising more than one delocalized, substituted pi-bonded moiety, only one thereof for each metal atom of the complex is a cyclic, delocalized, substituted pi-bonded moiety. The catalyst further comprises an activating cocatalyst.

Suitable cocatalysts for use herein include polymeric or oligomeric aluminoxanes, especially methyl aluminoxane, as well as inert, compatible, noncoordinating, ion forming compounds. So-called modified methyl aluminoxane (MMAO) is also suitable for use as a cocatalyst. One technique for preparing such modified aluminoxane is disclosed in U.S. Pat. No. 5,041,584, the disclosure of which is incorporated herein by reference. Aluminoxanes can also be made as disclosed in U.S. Pat. Nos. 5,218,071; 5,086,024; 5,041,585; 5,041,583; 5,015,749; 4,960,878; and 4,544,762, the disclosures of all of which are incorporated herein by reference.

Aluminoxanes, including modified methyl aluminoxanes, when used in the polymerization, are preferably used such that the catalyst residue remaining in the (finished) polymer is preferably in the range of from about 0 to about 20 ppm aluminum, especially from about 0 to about 10 ppm aluminum, and more preferably from about 0 to about 5 ppm aluminum. In order to measure the bulk polymer properties (e.g. PI or melt fracture), aqueous HCl is used to extract the aluminoxane from the polymer. Preferred cocatalysts, however, are inert, noncoordinating, boron compounds such as those described in EP 520732.

Substantially linear ethylene are produced via a continuous (as opposed to a batch) controlled polymerization process using at least one reactor (e.g., as disclosed in WO 93/07187, WO 93/07188, and WO 93/07189), but can also be produced using multiple reactors (e.g., using a multiple reactor configuration as described in U.S. Pat. No. 3,914,342, the disclosure of which is incorporated herein by reference) at a polymerization temperature and pressure sufficient to produce the interpolymers having the desired properties. The multiple reactors can be operated in series or in parallel, with at least one constrained geometry catalyst employed in at least one of the reactors.

Substantially linear ethylene polymers can be prepared via the continuous solution, slurry, or gas phase polymerization in the presence of a constrained geometry catalyst, such as the method disclosed in EP 416,815-A. The polymerization can generally be performed in any reactor system known in the art including, but not limited to, a tank reactor(s), a sphere reactor(s), a recycling loop reactor(s) or combinations thereof and the like, any reactor or all reactors operated partially or completely adiabatically, nonadiabatically or a combination of both and the like. Preferably, a continuous loop-reactor solution polymerization process is used to manufacture the substantially linear ethylene polymer used in the present invention.

In general, the continuous polymerization required to manufacture substantially linear ethylene polymers may be accomplished at conditions well known in the prior art for Ziegler-Natta or Kaminsky-Sinn type polymerization reactions, that is, temperatures from 0 to 250° C. and pressures from atmospheric to 1000 atmospheres (100 MPa). Suspension, solution, slurry, gas phase or other process conditions may be employed if desired.

A support may be employed in the polymerization, but preferably the catalysts are used in a homogeneous (i.e., soluble) manner. It will, of course, be appreciated that the active catalyst system forms in situ if the catalyst and the cocatalyst components thereof are added directly to the polymerization process and a suitable solvent or diluent, including condensed monomer, is used in said polymerization process. It is, however, preferred to form the active catalyst in a separate step in a suitable solvent prior to adding the same to the polymerization mixture.

The substantially linear ethylene polymers used in the present invention are interpolymers of ethylene with at least one $C_3$–$C_{20}$ α-olefin and/or $C_4$–$C_{18}$ diolefin. Copolymers of ethylene and an α-olefin of $C_3$–$C_{20}$ carbon atoms are especially preferred. The term "interpolymer" as discussed above is used herein to indicate a copolymer, or a terpolymer, or the like, where, at least one other comonomer is polymerized with ethylene or propylene to make the interpolymer.

Suitable unsaturated comonomers useful for polymerizing with ethylene include, for example, ethylenically unsaturated monomers, conjugated or non-conjugated dienes, polyenes, etc. Examples of such comonomers include $C_3$–$C_{20}$ α-olefins such as propylene, isobutylene, 1-butene, 1-hexene, 1-pentene, 4-methyl-1-pentene, 1-heptene, 1-octene, 1-nonene, 1-decene, and the like. Preferred comonomers include propylene, 1-butene, 1-pentene, 1-hexene, 4-methyl-1-pentene, 1-heptene, and 1-octene, and 1-octene is especially preferred. Other suitable monomers include styrene, halo- or alkyl-substituted styrenes, vinylbenzocyclobutane, 1,4-hexadiene, 1,7-octadiene, and naphthenics (e.g., cyclopentene, cyclohexene and cyclooctene).

In one preferred embodiment, the substantially hydrogenated block copolymer is blended with at least one polypropylene polymer. Suitable polypropylene polymers for use in the invention, including random block propylene ethylene polymers, are available from a number of manufacturers, such as, for example, Montell Polyolefins and Exxon Chemical Company. At Exxon, suitable polypropylene polymers are supplied under the designations ESCORENE and ACHIEVE.

Suitable poly lactic acid (PLA) polymers for use in the invention are well known in the literature (e.g., see D. M. Bigg et al., "Effect of Copolymer Ratio on the Crystallinity and Properties of Polylactic Acid Copolymers", ANTEC '96, pp. 2028–2039; WO 90/01521; EP 0 515203A; and EP 0 748846A2. Suitable poly lactic acid polymers are supplied commercially by Cargill Dow under the designation Eco-PLA.

Suitable thermoplastic polyurethane polymers for use in the invention are commercially available from The Dow Chemical Company under the designation PELLATHANE.

Suitable polyolefin carbon monoxide interpolymers can be manufactured using well known high pressure free-radical polymerization methods. However, they may also be manufactured using traditional Ziegler-Natta catalysis and even with the use of so-called homogeneous catalyst systems such as those described and referenced herein above.

Suitable free-radical initiated high pressure carbonyl-containing ethylene polymers such as ethylene acrylic acid interpolymers can be manufactured by any technique known in the art including the methods taught by Thomson and Waples in U.S. Pat. No. 3,520,861 and by McKinney et al. in U.S. Pat. Nos. 4,988,781; 4,599,392; and 5,384,373, the disclosures of which are incorporated herein by reference.

Suitable ethylene vinyl acetate interpolymers for use in the invention are commercially available from various suppliers, including Exxon Chemical Company and Du Pont Chemical Company.

Suitable ethylene/alkyl acrylate interpolymers are commercially available from various suppliers. Suitable ethylene/acrylic acid interpolymers are commercially available from The Dow Chemical Company under the designation PRIMACOR. Suitable ethylene/methacrylic acid interpolymers are commercially available from Du Pont Chemical Company under the designation NUCREL.

Chlorinated polyethylene (CPE), especially chlorinated substantially linear ethylene polymers, can be prepared by chlorinating polyethylene in accordance with well known techniques. Preferably, chlorinated polyethylene comprises equal to or greater than 30 weight percent chlorine. Suitable chlorinated polyethylenes for use in the invention are commercially supplied by The Dow Chemical Company under the designation TYRIN.

Additives e.g., Irgafos® 168 or Irganox® 1010 supplied by Ciba Geigy Corp., may be added to the composition and blends thereof to protect against undo degradation during shaping or fabrication operation or to better control the extent of grafting or crosslinking (i.e., inhibit excessive gelation). In-process additives, e.g. calcium stearate, water, and fluoropolymers may also be used for purposes such as for the deactivation of residual catalyst or for further improved processability.

Formulated Systems

The term "formulated system" as used herein means the combination of at least one substantially hydrogenated block copolymer with at least one low molecular viscosity-reducing additive. Suitable low molecular weight viscosity-reducing additives include, for example, but not limited to, oils (preferably paraffinic oils), waxes (preferably a paraffinic waxes), processing aids (e.g. stearates and fluoropolymers) and tackifiers (e.g. hydrocarbons, rosins and terpenes).

In one embodiment, the composition used to produce the fibers or articles of the present invention is a formulated system comprising (A) at least one substantially hydrogenated block copolymer characterized as having i) a weight ratio of conjugated diene monomer unit to vinyl aromatic monomer unit before hydrogenation of greater than or equal to 60:40;

ii) a weight average molecular weight ($M_w$) before hydrogenation of from about 30,000 to about 150,000, wherein each vinyl aromatic monomer unit (A) has a weight average molecular weight, $Mw_a$, of from about 5,000 to about 45,000 and each conjugated diene monomer unit (B) has a weight average molecular weight, $Mw_b$, of from about 12,000 to about 110,000; and iii) a hydrogenation level such that each vinyl aromatic monomer unit block is hydrogenated to a level of greater than 90 percent and each conjugated diene monomer unit block is hydrogenated to a level of greater than 95 percent, as determined using UV-VIS spectrophotometry and proton NMR analysis; and (B) an oil; and optionally, (C) from about 0 to about 60 weight percent of polyolefin having a weight average molecular weight greater than 10,000, preferably greater than 20,000, more preferably greater than 30,000, as determined using gel permeation chromatography;

(D) from about 0 to about 40 weight percent of a wax; and (E) from about 0 to about 50 weight percent of a tackifier.

In certain embodiments, especially at molecular weights greater than 81,500, at least one substantially hydrogenated block copolymer is formulated with oil, wax, processing aid, plasticizer, or tackifier or all of these (i.e. the inventive formulated system) for improved melt drawability and fiber spinnability.

The term "tackifier" as used herein means any of several compositions or compounds which tack or adhesiveness to polymer compositions. Representative classes of tackifiers include aliphatic $C_5$ resins, polyterpene resins, hydrogenated resins, mixed aliphatic-aromatic resins, rosin esters, and hydrogenated rosin esters. The tackifier employed will typically have a viscosity at 350° F., as measured using a Brookfield viscometer, of no more than 300, preferably no more than 150, and most preferably no more than 50 centipoise. The tackifier employed will typically have a glass transition temperature greater than 50° C.

Suitable aliphatic tackifiers for use in the present invention include those available under the trade designations Escorez™, Piccotac™, Mercures™, Wingtack™, Hi-Rez™, Quintone™, and Tackirol™. Suitable polyterpene tackifiers include those available under the trade designations Nirez™, Piccolyte™, Wingtack™, and Zonarez™. Suitable hydrogenated tackifiers include those available under the trade designations Escorez™, Arkon™, and Clearon™. Suitable mixed aliphatic-aromatic tackifiers include those available under the trade designations Escorez™, Regalite™, Hercures™, AR™, Imprez™, Norsolene™ M, Marukarez™, Arkon™ M, Quintone™, etc. Other tackifiers may be employed, provided they are compatible with the substantially hydrogenated block copolymer.

The tackifier will be present in the formulated system of the invention in an amount less than 70 weight percent, preferably less than 50 weight percent, more preferably less than 25 weight percent and in some instances, less than 10 weight percent tackifiers may be employed.

The term "wax" is used herein to refer to paraffinic or crystalline polymers having a number average molecular weight less than 6000. Exemplary polymers falling within this category include ethylene homopolymers available from Petrolite, Inc. (Tulsa, Okla.) as Polywax™ 500, Polywax™ 1500 and Polywax™ 2000; and paraffinic waxes available from CP Hall under the product designations 1230, 1236, 1240,1245, 1246,1255, 1260, and 1262.

Polywax™ 2000 has a molecular weight of approximately 2000, an $M_w/M_n$ of approximately 1.0, a density at 16° C. of about 0.97 g/cm³, and a melting point of approximately 126° C.

CP Hall 1246 paraffinic wax is available from CP Hall (Stow, Ohio). CP Hall 1246 paraffinic wax has a melting point of 143° F., a Brookfield viscosity at 210° F. of 4.2 centipoise, and a specific gravity at 73° F. of 0.915.

Preferred waxes will be prepared using a constrained geometry catalyst. Such polymers will be either ethylene homopolymers or interpolymers of ethylene and a comonomer such as, for example, $C_3$–$C_{20}$ α-olefins, styrene, alkyl-substituted styrene, tetrafluoroethylene, vinylbenzocyclobutane, non-conjugated dienes, and naphthenics. Such polymers, in contrast to traditional waxes, will have an $M_w/M_n$ of from 1.5 to 2.5, preferably from 1.8 to 2.2. Such polymers are disclosed and claimed in the application entitled "Ultra-Low Molecular Weight Ethylene Polymers", filed on Jan. 22, 1996 as Provisional Application 60/010403 in the names of Finlayson, et al.

Suitable waxes for use in the formulated system have a number average molecular weight less than 6000, preferably less than 5000 and greater than 800, preferably greater than 1300.

Suitable ethylene polymer waxes, i.e., an ethylene homopolymer (either a traditional ethylene homopolymer wax or an ethylene homopolymer prepared with a constrained geometry catalyst) or an interpolymer of ethylene and a comonomer selected from the group consisting of $C_3$–$C_{20}$ α-olefins, non-conjugated dienes, and naphthenics, will have a density of at least 0.910 g/cm³ and no more than 0.970 g/cm³, preferably no more than 0.965 g/cm³.

The term "oil" is used herein in its conventional sense to refer to fats, viscous liquids, and volatile liquids which are classified as mineral, vegetable, animal, essential or edible oil. When employed, oils will be present in an amount less than 25, preferably less than 15, and more preferably less than 10 weight percent, based on the weight of the hot melt adhesive. Exemplary oils include white mineral oil (such as Kaydol™ oil available from Witco), and Shellflex™ 371 naphthenic oil (available from Shell Oil Company). Preferred oils are white mineral paraffinic oils such as, for example, Witco 200 process oil supplied by Witco Chemical Corporation.

The composition comprising the substantially hydrogenated block copolymer can be filled or unfilled. If filled, then the amount of filler present should not exceed an amount that would adversely affect elevated temperature elasticity. Typically, the amount of filler present is between about 20 and about 80, preferably between about 50 and about 70, weight percent (wt. percent) based on the total weight of the interpolymer. Representative fillers include kaolin clay, magnesium hydroxide, silica, calcium carbonate. In a preferred embodiment, in which a filler is present, the filler is coated with a material that will prevent or retard any tendency that the filler might otherwise have to interfere with the crosslinking reactions. Stearic acid is illustrative of such a filler coating.

The formulated system surprisingly shows significantly higher tensile strength while maintaining good processability, as indicated by higher melt flow rates, relative to a formulated partially hydrogenated block copolymer system. In other words, the formulated system exhibits significantly improved processability at equivalent tensile strength relative to comparative formulated systems.

The fibers and articles of the present invention have utility in a variety of applications. Suitable applications include, for example, but are not limited to, disposable personal hygiene products (e.g. training pants, diapers, absorbent underpants, incontinence products, feminine hygiene items and the like); disposable garments (e.g. industrial apparel, coveralls, head coverings, underpants, pants, shirts, gloves, socks and the like); infection control/clean room products (e.g. surgical gowns and drapes, face masks, head coverings, surgical caps and hood, shoe coverings, boot slippers, wound dressings, bandages, sterilization wraps, wipers, lab coats, coverall, pants, aprons, jackets, bedding items and sheets and the like) and sports apparel.

Various homofil fibers can be made including staple fibers, spunbond fibers or melt blown fibers (using, e.g., systems as disclosed in U.S. Pat. No. 4,340,563 (Appel et al.), U.S. Pat No. 4,663,220 (Wisneski et al.), U.S. Pat. No. 4,668,566 (Braun), or U.S. Pat. No. 4,322,027 (Reba), all of which are incorporated herein by reference), and gel spun fibers (e.g., the system disclosed in U.S. Pat. No. 4,413,110 (Kavesh et al.), incorporated herein by reference)). The term "homofil" as used herein refers to fiber which has a single polymer region or domain and does not have any other distinct polymer regions (as do bicomponent fibers), even though the polymer itself may have a plurality of phases or microphases.

Staple fibers can be melt spun (i.e., they can be extruded into the final fiber diameter directly without additional drawing), or they can be melt spun into a higher diameter and subsequently hot or cold drawn to the desired diameter using conventional fiber drawing techniques.

The fibers of the present invention can also be used as bonding fibers, especially where the fibers of the present invention have a lower melting point than the surrounding matrix fibers. In a bonding fiber application, the bonding fiber is typically blended with other matrix fibers and the entire structure is subjected to heat, where the bonding fiber melts and bonds the surrounding matrix fiber. Typical matrix fibers which benefit from use of the inventive elastic fibers disclosed herein include, but are not limited to, poly (ethylene terephthalate) fibers, cotton fibers, nylon fibers, polypropylene fibers, heterogeneously branched polyethylene fibers, homogeneously branched ethylene polymer fibers, linear polyethylene homopolymer fibers and the like and combinations thereof. The diameter of the matrix fiber can vary depending upon the end use application.

Conjugated fibers are also an aspect of the present invention. The term "conjugated fibers" refers to fibers which have been formed from at least two polymers extruded from separate extruders but meltblown or spun together to form one fiber. Conjugated fibers are sometimes referred to in the art as multicomponent or bicomponent fibers. The polymers are usually different from each other although conjugated fibers may be monocomponent fibers. The polymers are arranged in substantially constant positioned distinct zones across the cross-section of the conjugated fibers and extend continuously along the length of the conjugated fibers. The configuration of conjugated fibers can be, for example, a sheath/core arrangement (wherein one polymer is surrounded by another), a side by side arrangement, a pie arrangement or an "islands-in-the sea" arrangement. Conjugated fibers are described in U.S. Pat. No. 5,108,820 to Kaneko et al.; U.S. Pat. No. 5,336,552 to Strack et al.; and U.S. Pat. No. 5,382,400 to Pike et al., the disclosures of all of which are incorporated herein by reference. The elastic fiber of the present invention can be in a conjugated configuration, for example, as a core or sheath, or both.

Such bicomponent fibers comprise the substantially hydrogenated block copolymer composition in at least one portion of the fiber. For example, in a sheath/core bicomponent fiber (i.e., one in which the sheath concentrically surrounds the core), the elastic material can be in either the sheath or the core. Other types of bicomponent fibers are within the scope of the invention as well, and include such structures as side-by-side conjugated fibers (e.g., fibers having separate regions of polymers, wherein the elastic material of the present invention comprises at least a portion of the fiber's surface).

The shape of the fiber is not limited. For example, typical fiber has a circular cross-sectional shape, but sometimes fibers have different shapes, such as a trilobal shape, or a flat (i.e., "ribbon" like) shape. The elastic fiber disclosed herein is not limited by the shape of the fiber.

The novel elastic fiber of the present invention can be used with other fibers such as PET, Nylon, and cotton to make elastic fabrics.

Fiber diameter can be measured and reported in a variety of fashions. Generally, fiber diameter is measured in denier per filament. Denier is a textile term which is defined as the grams of the fiber per 9000 meters of that fiber's length. Monofilament generally refers to an extruded strand having a denier per filament greater than 15, usually greater than 30. Fine denier fiber generally refers to fiber having a denier of about 15 or less. Microdenier (aka microfiber) generally refers to fiber having a diameter not greater than about 100 micrometers. For the inventive elastic fibers disclosed herein, the diameter can be widely varied, with little impact upon the fiber's elasticity. But the fiber denier can be adjusted to suit the capabilities of the finished article and as such, would preferably be: from about 0.5 to about 30 denier/filament for melt blown; from about 1 to about 30 denier/filament for spunbond; and from about 1 to about 20,000 denier/filament for continuous wound filament. Nonetheless, preferably, the nominal denier is greater than 37, more preferably greater than or equal to 55 and most preferably greater than or equal to 65. These preferences are due to the fact that typically durable apparel employ fibers with deniers greater than or equal to about 40.

The term "meltblown" is used herein in the conventional sense to refer to fibers formed by extruding a molten composition through a plurality of fine, usually circular, die capillaries as molten threads or filaments into converging high velocity gas streams (e.g. air) which function to attenuate the threads or filaments to reduced diameters. Thereafter, the filaments or threads are carried by the high velocity gas streams and deposited on a collecting surface to form a web of randomly dispersed fibers with average diameters generally smaller than 10 microns.

The term "spunbond" is used herein in the conventional sense to refer to fibers formed by extruding a molten composition as filaments through a plurality of fine, usually circular, die capillaries of a spinneret with the diameter of the extruded filaments then being rapidly reduced and thereafter depositing the filaments onto a collecting surface to form a web of randomly dispersed spunbond fibers with average diameters generally between about 7 and about 30 microns.

The term "nonwoven" as used herein and in the conventional sense means a web or fabric having a structure of individual fibers or threads which are randomly interlaid, but not in an identifiable manner as is the case for a knitted fabric. The elastic fiber of the present invention can be employed to prepare inventive nonwoven elastic fabrics as well as composite structures comprising the elastic nonwoven fabric in combination with nonelastic materials.

Fabrics made from the inventive elastic fibers disclosed herein include both woven and nonwoven fabrics. Nonwoven fabrics can be made variously, including spunlaced (or hydrodynamically entangled) fabrics as disclosed in U.S. Pat. No. 3,485,706 (Evans) and U.S. Pat. No. 4,939,016 (Radwanski et al.), the disclosures of which are incorporated herein by reference; by carding and thermally bonding staple fibers; by spunbonding continuous fibers in one continuous operation; or by melt blowing fibers into fabric and subsequently calendering or thermally bonding the resultant web. These various nonwoven fabric manufacturing techniques are well known to those skilled in the art and the disclosure is not limited to any particular method. Other structures made from such fibers are also included within the scope of the invention, including e.g., blends of these novel fibers with other fibers (e.g., poly(ethylene terephthalate) (PET) or cotton).

The term "thermal bonding" as used herein refers to the heating of fibers to effect the melting (or softening) and fusing of fibers such that a nonwoven fabric is produced. Thermal bonding includes calendar bonding and through-air bonding as well as methods known in the art.

The expression "thermal bondable at a reduced hot melt adhesive amount" refers to comparative peel test results using Ato Findley Adhesive HX9275 (supplied by Ato Findley Nederlands B. V., Roosendaal, The Netherlands) or H. B. Fuller Adhesive D875BD1 (supplied by H. B. Fuller GmbH, I-Oneburg, Germany) and test procedures and methods described in WO 00/00229, wherein the same peel strength as the adhesive without deploying thermal bonding can be obtained even though the quantity of adhesive is at least 15 percent less where thermal bonding is deployed.

Fabricated articles which can be made using the inventive elastic fibers and fabrics disclosed herein include elastic composite articles (e.g., diapers) that have elastic portions. For example, elastic portions are typically constructed into diaper waist band portions to prevent the diaper from failing and leg band portions to prevent leakage (as shown in U.S. Pat. No. 4,381,781 (Sciaraffa), the disclosure of which is incorporated herein by reference). Often, the elastic portions promote better form fitting and/or fastening systems for a good combination of comfort and reliability. The inventive elastic fibers and fabrics disclosed herein can also produce structures which combine elasticity with breathability. For example, the inventive elastic fibers, fabrics or films or all of these of the present invention many be incorporated into the structures disclosed in U.S. provisional patent application 60/083,784, filed May 1, 1998 in name Maugans et al., the disclosure of which is incorporated herein by reference.

The term "elastic article" is used in reference to shaped items produced from the elastic fibers of the present invention.

The term "elastic" or "elastic-like behavior" as used herein refers to any material having a permanent set less than or equal to 60 percent, especially less than or equal to 50 percent and most especially less than or equal 25 percent (i.e. most especially greater than or equal to 87.5 percent recovery) at 200 percent strain and at a temperature between its glass transition temperature and its crystalline melting point or range is stretchable to a stretched, biased length at least 200 percent greater than its relaxed, unstretched length. The extent that a material does not return to its original dimensions after being stretched is its percent permanent set.

Elastic polymeric materials are also referred to in the art as "elastomers" and "elastomeric" and materials with a permanent set of less than 10 percent when stretched to a stretched, biased length of at least 200 percent greater their original relaxed, unstretched lengths are considered "highly elastic".

An absorbent article can comprise one or more of the various fluid handling members, such as one or more fluid acquisition member, one or more fluid distribution members and/or one or more fluid storage members or a combination acquisition/distribution layer. Each of these members can comprise one or more sub-elements, which can be homogeneous or not, e.g. each member can be made from the same material but in different forms or they can be made from several materials.

For example, such members can be layers, optionally consisting of sub-layers, and or optionally having different composition, or density, or thickness.

Each of these members can have a specialized functionality, such as primarily providing acquisition functionality or primarily providing fluid storage functionality.

Alternatively, members can have multiple functionality, such as the very first "cellulose only" diapers wherein the cellulose fluff performed acquisition, distribution and ultimate storage functionality at the same time.

The "storage absorbent member" refers to the absorbent member(s) of the absorbent core that function primarily to ultimately store absorbed fluids.

A "fluid distribution member" in the meaning of the present invention is a member, which satisfies the requirements as laid out for the fluid distribution functionality, regardless whether the member also has some other fluid handling functionality.

A "fluid acquisition member" refers to parts or the absorbent core, which are primarily designed to receive liquid as it reaches the absorbent article.

A "acquisition distribution layer or member" refers to that member of the absorbent article or item that primarily functions to receive liquid as it reaches the absorbent article or item and transfers the received liquid to the storage member of the article or item.

As used herein, the term "absorbent core material" refers to the member of the absorbent article that is primarily responsible for fluid handling of the article, thus including the "fluid handling member(s)". As such, the absorbent core material typically does not include the topsheet or backsheet of the absorbent article, though in certain instances the topsheet could be considered, for example, to provide specific fluid acquisition performance.

An absorbent core can be divided into "regions" of the core, wherein such "regions" can perform the functionality of one or more of the members as outlined above. Thus, an acquisition region can comprise an acquisition member (and also comprise other members), it can consist of an acquisition member (and nothing else), which can consist of an acquisition material. Or, an acquisition/distribution region can comprise both an acquisition member and a distribution member.

As used herein, the term "absorbent articles" refers to devices which absorb and contain body exudates, and, more specifically, refers to devices which are placed against or in proximity to the body of the wearer to absorb and contain the various exudates discharged from the body. As used herein, the term "body fluids" includes but is not limited to urine, menses, vaginal discharges, sweat and feces.

The term "disposable" is used herein to describe articles or items that are not intended to be laundered or otherwise restored or reused as originally provided (i.e., they are intended to be discarded after use and, preferably, to be recycled, composted or otherwise disposed of in an environmentally compatible manner).

As used herein, the terms "region(s)" or "zone(s)" refer to portions or sections of the absorbent member. Thereby, the region(s) or zone(s) can be two-dimensional (front/back) or can be three-dimensional (like an acquisition region having—even if it were in the form of a layer—a three-dimensional extension).

As use herein, the term "layer" refers to an absorbent member whose primary dimension is X-Y, i.e., along its length and width. It should be understood that the term layer is not necessarily limited to single layers or sheets of material. Thus the layer can comprise laminates or combinations of several sheets or webs of the requisite type of materials. Accordingly, the term "layer" includes the terms "layers" and "layered".

For purposes of this invention, the term "upper" should be understood to refer to absorbent members, such as layers, that are nearest to the wearer of the absorbent article, and typically face the topsheet of an absorbent article; conversely, the term "lower" refers to absorbent members that are furthermost away from the wearer of the absorbent article and typically face the backsheet.

The "superabsorbent polymer" is used herein in the conventional sense in reference to polymeric materials that imbibe fluid and thereby form a swollen hydrogel. That is, a superabsorbent polymer is a hydrogel-forming polymeric gelling agent. In particular, the polymeric gelling agent comprises a substantially water-insoluble, slightly crosslinked, partially neutralized, hydrogel-forming polymer material that is typically prepared from polymerizable, unsaturated, acid-containing monomers and often grafted onto other types of polymer moieties and then slightly crosslinked with agents such as, for example, triallyl amine. See, for example, U.S. Pat. Nos. 5,061,259 and 4,654,039, the disclosures of which are incorporated herein by reference, for additional description pertaining to superabsorbent polymers. Superabsorbent polymer is referenced herein by the acronym "SAP".

Preferably, an elastic article is fabricated using an extrusion technique (i.e., the method consists of melting the inventive block polymer). Suitable extrusion techniques include, but are not limited to, fiber melt spinning, fiber melt blowing, film blowing, cast film, injection molding, blow molding, profile extrusion, or rotomolding techniques.

The inventive elastic fibers and fabrics disclosed herein can also be used in various structures as described in U.S. Pat. No. 2,957,512 (Wade), the disclosure of which is incorporated herein by reference. For example, layer 50 of the structure described in U.S. Pat. No. '512 (i.e., the elastic component) can be replaced with the inventive elastic fibers and fabrics, especially where flat, pleated, creped, or crimped nonelastic materials are made into elastic structures. Attachment of the inventive elastic fibers or fabric disclosed herein to nonelastic fibers, fabrics or other structures can be done by melt bonding or with adhesives. Gathered or shirred elastic structures can be produced from the inventive elastic fibers or fabrics disclosed herein and nonelastic components by pleating the non-elastic component (as described in U.S. Pat. No. '512) prior to attachment, pre-stretching the elastic component prior to attachment, or heat shrinking the elastic component after attachment.

The inventive elastic fibers described herein also can be used in a spunlaced (or hydrodynamically entangled) process to make novel structures. For example, U.S. Pat. No. 4,801,482 (Goggans), the disclosure of which is incorporated herein by reference, discloses an elastic sheet (12) which can now be made with the novel elastic fibers/fabric described herein.

Continuous elastic filaments as described herein could also be used in woven applications where high resilience is desired.

The inventive elastic fibers and fabrics disclosed herein with adjustments in molecular weight or degree of crosslinking or extent or radiation or all of these also have adjustable tenacity and retractive force. Such capabilities and characteristics enable extensive design flexibility, for example, to provide for variable retractive forces in the same garment, if needed, as described for example in U.S. Pat. No. 5,196,000 (Clear et al.), the disclosure of which is incorporated herein by reference.

U.S. Pat. No. 5,037,416 (Allen et al.), the disclosure of which is incorporated herein by reference, describes the advantages of a form fitting top sheet by using elastic ribbons (see member 19 of U.S. Pat. No. '416). The inventive elastic fibers could serve the function of member 19 of U.S. Pat. No. '416, or could be used in fabric form to provide the desired elasticity.

Composites that utilize very high molecular weight linear polyethylene or copolymer polyethylene also benefit from the inventive elastic fibers disclosed herein. For example, a blend of inventive elastic fibers disclosed herein with a very high molecular weight polyethylene fibers (e.g., Spectra™ fibers made by Allied Chemical) as described in U.S. Pat. No. 4,584,347 (Harpell et al.), the disclosure of which is incorporated herein by reference, may provide bonding through the fibers without melting the high molecular weight fibers, thus preserving the high strength and integrity of the high molecular weight fiber.

As described in U.S. Pat. No. 4,981,747 (Morman), disclosure of which is incorporated herein by reference, the inventive elastic fibers or fabrics disclosed herein can be substituted for elastic sheet 122, which forms a composite elastic material including a reversibly necked material.

The inventive elastic fibers disclosed herein can also be a melt blown elastic component, as described in reference 6 of the drawings of U.S. Pat. No. 4,879,170 (Radwanski), the disclosure of which is incorporated herein by reference. U.S. Pat. No. '170 generally describes elastic co-form material and manufacturing processes.

Elastic panels can also be made from the inventive elastic fibers and fabrics disclosed herein, and can be used, for example, as members 18, 20, 14, and/or 26 of U.S. Pat. No. 4,940,464 (Van Gompel), the disclosure of which is incorporated herein by reference. The inventive elastic fibers and fabrics described herein can also be used as elastic components of composite side panels (e.g., layer 86 of U.S. Pat. No. '464).

Fabricated articles which can be made using the inventive elastic articles disclosed herein include composite fabric articles (e.g., disposable incontinence garments, training pants and diapers, especially pull-up diapers) that are comprised of one or more elastic component or portion. Inventive examples are such uses may follow the teachings of Kieffer et al. in U.S. Pat. No. 4,789,699. The inventive elastic articles disclosed herein can also produce fabric composite structures which combine elasticity with breathability by utilizing a technique that renders the elastic material pervious or "breathable" such as suggested by Lippert et al. in U.S. Pat. No. 4,861,652 and indicated above.

The inventive elastic articles disclosed herein can also be used in various structures as described in U.S. Pat. No. 2,957,512 (Wade), the disclosure of which is incorporated herein by reference.

The inventive elastic articles described herein can also be used to make other novel structures. For example, U.S. Pat. No. 4,801,482 (Goggans), the disclosure of which is incorporated herein by reference, discloses an elastic sheet (12) which can now be made with the inventive elastic articles described herein.

The inventive elastic articles described herein can also be used to make breathable portion or breathable elastic composite materials. For example, U.S. Pat. No. 5,085,654 (Buell) discloses a leg band (15) with a breathable portion 45, a breathable topsheet (26), a breathable backsheet (25), elastic elements (31 and 64), a breathable element (54), and a breathable sub-element (96) all or any combination of which can now be made with the inventive elastic articles disclosed herein in either pervious or impervious forms.

U.S. Pat. No. 5,037,416 (Allen et al.), the disclosure of which is incorporated herein by reference, describes the advantages of a form fitting top sheet by using elastic ribbons (member 12) and an elastic backsheet (member 16).

Pervious inventive elastic articles described herein could serve the function of member 12.

In U.S. Pat. No. 4,981,747 (Morman), the inventive elastic articles disclosed herein can be substituted for elastic sheets 12, 122 and 232 to construct an elastic composite material which includes a reversibly necked material.

Elastic panels, elements, portions or the like can also be made from the inventive elastic articles disclosed herein, and can be used, for example, as members 18, 20, 24, and/or 26 of U.S. Pat. No. 4,940,464 (Van Gompel), the disclosure of which is incorporated herein by reference. The inventive elastic articles described herein can also be used, for example, as elastic composite side panels (e.g., layer) or as elastic ribbons 42 and/or 44.

Curing, Irradiation and Crosslinking

In the practice of the present invention, curing, irradiation or crosslinking of the fibers or articles can be accomplished by any means known in the art, including, but not limited to, electron-beam irradiation, beta irradiation, X-rays, gamma irradiation, controlled thermal heating, corona irradiation, peroxides, allyl compounds and UV radiation with or without crosslinking catalyst. Electron-beam irradiation is the preferred technique for crosslinking. Preferably, the curing, irradiation, crosslinking or combination thereof provides a percent gel, as determined using xylene in accordance with ASTM D-2765, of greater than or equal to 40 weight percent, more preferably greater than or equal to 50 weight percent, most preferably greater than or equal to 70 weight percent.

The term "radiated" or "irradiated" as used herein refers to exposure to at least 3 megarads (or the equivalent thereof) of radiation dosage whether or not there was a measurable decrease in percent xylene extractables (i.e., increase in insoluble gel). That is, substantial crosslinking may not result from the irradiation.

Suitable electron-beam irradiation equipment is available from Energy Services, Inc. Wilmington, Mass. with capabilities of at least 100 kilo-electron volts (KeV) and at least 5 kilowatts (Kw). Preferably, electrons are employed up to 70 megarads dosages. The irradiation source can be any electron beam generator operating in a range of about 150 Kev to about 6 mega-electron volts (MeV) with a power output capable of supplying the desired dosage. The electron voltage can be adjusted to appropriate levels which may be, for example, 100,000, 300,000, 1,000,000 or 2,000,000 or 3,000,000 or 6,000,000 or higher or lower. Many other apparati for irradiating polymeric materials are known in the art. The irradiation is usually carried out at a dosage between about 3 megarads to about 35 megarads, preferably between about 8 to about 30 megarads, more preferably between about 8 to about 20 megarads. Further, the irradiation can be carried out conveniently at room temperature, although higher and lower temperatures, for example 0° C. to about 60° C., may also be employed.

The irradiation can be carried out on-line (i.e. during fabrication of the article), off-line (such as after fabrication of the article, for example, film, by unwinding or wrapping the fabricated article) or on-spool (as such in the case of fibers, filaments and the like). Preferably, the irradiation is carried out after shaping or fabrication of the article. Also, in a preferred embodiment, a pro-rad additive is incorporated into the composition and the composition is subsequently irradiated with electron beam radiation at about 8 to about 30 megarads.

In another aspect of the invention, the irradiation (preferably electron beam irradiation) is carried out under an inert atmosphere. Suitable atmospheres can be provided by the use of helium, argon, or nitrogen. Substantial improvements in high temperature serviceability can be gained by using an inert atmosphere without any attendant substantial lost in elastic performance ordinarily associated with service or use at elevated temperatures.

The terms "crosslinked" and "substantially crosslinked" as used herein mean the fiber or the article of the present invention is characterized as having xylene extractables of less than or equal to 70 weight percent (that is, greater than or equal to 30 weight percent gel content), preferably less than or equal to 40 weight percent (that is, greater than or equal to 60 weight percent gel content), where xylene extractables (and gel content) are determined in accordance with ASTM D-2765.

The terms "cured" and "substantially cured" as used herein means the fiber or the article of the present invention was subjected or exposed to a treatment which induced crosslinking. As used herein, the terms relate to the use of a grafted silane compound.

The terms "curable" and "crosslinkable" as used herein mean the fiber or the article of the present invention is not crosslinked and has not been subjected or exposed to treatment which induces crosslinking although the composition used to produce the fiber or the article of the present invention comprises additive(s) or functionality which will effectuate crosslinking upon subjection or exposure to such treatment.

Crosslinking can be promoted with a crosslinking catalyst, and any catalyst that will provide this function can be used. Suitable catalysts generally include organic bases, carboxylic acids, and organometallic compounds including organic titanates and complexes or carboxylates of lead, cobalt, iron, nickel, zinc and tin. Dibutyltindilaurate, dioctyltinmaleate, dibutyltindiacetate, dibutyltindioctoate, stannous acetate, stannous octoate, lead naphthenate, zinc caprylate, cobalt naphthenate; and the like. Tin carboxylate, especially dibutyltindilaurate and dioctyltinmaleate, are particularly effective for this invention. The catalyst (or mixture of catalysts) is present in a catalytic amount, typically between about 0.015 and about 0.035 phr.

The term "pro-rad additive" as used herein means a compound which is not activated during normal fabrication or processing of the composition, but can be activated by the application of temperatures (heat) substantial above normal fabrication or processing temperatures or ionizing energy (or both) to effectuate some measurable gelation or preferably, substantial crosslinking.

Representative pro-rad additives include, but are not limited to, azo compounds, organic peroxides and polyfunctional vinyl or allyl compounds such as, for example, triallyl cyanurate, triallyl isocyanurate, pentaerythritol tetramethacrylate, glutaraldehyde, ethylene glycol dimethacrylate, diallyl maleate, dipropargyl maleate, dipropargyl monoallyl cyanurate, dicumyl peroxide, di-tert-butyl peroxide, t-butyl perbenzoate, benzoyl peroxide, cumene hydroperoxide, t-butyl peroctoate, methyl ethyl ketone peroxide, 2,5-dimethyl-2,5-di(t-butyl peroxy)hexane, lauryl peroxide, tert-butyl peracetate, azobisisobutyl nitrite and the like and combination thereof. Preferred pro-rad additives for use in the present invention are compounds which have poly-functional (i.e. at least two) moieties such as C=C, C=N or C=O.

At least one pro-rad additive can be introduced to the hydrogenated block copolymer by any method known in the art. However, preferably the pro-rad additive(s) is introduced via a masterbatch concentrate comprising the same or different base resin as the hydrogenated block copolymer.

Preferably, the pro-rad additive concentration for the masterbatch is relatively high e.g., about 25 weight percent (based on the total weight of the concentrate).

The at least one pro-rad additive is introduced to the hydrogenated block copolymer in any effective amount. Preferably, the at least one pro-rad additive introduction amount is from about 0.001 to about 5 weight percent, more preferably from about 0.005 to about 2.5 weight percent and most preferably from about 0.015 to about 1 weight percent (based on the total weight of the substantially hydrogenated block copolymer).

The composition comprising hydrogenated block copolymer may be crosslinked or cured by first grafting a silane onto its polymer backbone and thereafter subjecting or exposing the silane grafted polymer to water or atmospheric moisture. Preferably, the silane grafted polymer is subjected or exposed to water or atmospheric moisture after a shaping or fabrication operation.

Suitable silanes for silane crosslinking include those of the general formula

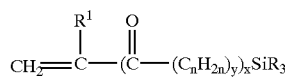

in which $R^1$ is a hydrogen atom or methyl group; x and y are 0 or 1 with the proviso that when x is 1, y is 1; n is an integer from 1 to 12 inclusive, preferably 1 to 4, and each R independently is a hydrolyzable organic group such as an alkoxy group having from 1 to 12 carbon atoms (e.g. methoxy, ethoxy, butoxy), aryloxy group (e.g. phenoxy), aryloxy group (e.g. benzyloxy), aliphatic acyloxy group having from 1 to 12 carbon atoms (e.g. formyloxy, acetyloxy, propanoyloxy), amino or substituted amino groups (alkylamino, arylamino), or a lower alkyl group having 1 to 6 carbon atoms inclusive, with the proviso that not more than one of the three R groups is an alkyl.

Suitable silanes may be grafted by the use of a suitable quantity of organic peroxide, either before or during a shaping or fabrication operation. However, preferably, the silane is grafted onto a hydrogenated block copolymer blend component before shaping or fabrication operations. In any case, the curing or crosslinking reaction takes place following the shaping or fabrication operation by reaction between the grafted silane groups and water. The water permeating into the bulk polymer from the atmosphere or from a water bath or "sauna". The phase of the process during which the crosslinks are created is commonly referred to as the "cure phase" and the process itself is commonly referred to as "curing".

Any silane that effectively grafts to and crosslinks the composition or its blend components can be used in the present invention. Suitable silanes include unsaturated silanes that comprise an ethylenically unsaturated hydrocarbyl group, such as a vinyl, allyl, isopropenyl, butenyl, cyclohexenyl or γ-(meth)acryloxy allyl group, and a hydrolyzable group, such as, for example, a hydrocarbyloxy, hydrocarbonyloxy, or hydrocarbylamino group. Examples of hydrolyzable groups include methoxy, ethoxy, formyloxy, acetoxy, proprionyloxy, and alkyl or arylamino groups. Preferred silanes are the unsaturated alkoxy silanes which can be grafted onto the polymer. These silanes and their method of preparation are more fully described in U.S. Pat. No. 5,266,627 to Meverden, et al., the disclosure of which is incorporated herein by reference. Vinyl trimethoxy silane, vinyl triethoxy silane, γ-(meth)acryloxy propyl trimethoxy silane and mixtures of these silanes are the preferred silane crosslinkers for use in this invention. If a filler is present, then preferably the crosslinker includes vinyl triethoxy silane.

The amount of silane crosslinker used in the present invention can vary widely depending several factors such as the silane itself, processing conditions, grafting efficiency, organic peroxide selection, the ultimate application, and similar factors. However, typically at least 0.5, preferably at least 0.7, parts per hundred resin (phr) is used. Considerations of convenience and economy are usually the two principal limitations on the maximum amount of silane crosslinker used, and typically the maximum amount of silane crosslinker does not exceed 5, preferably it does not exceed 2, phr. As used in parts per hundred resin or phr, "resin" means the hydrogenated block copolymer.

The silane crosslinker is grafted by any conventional method, typically in the presence of a free radical initiator e.g. peroxides and azo compounds, or by ionizing radiation, etc. A suitable grafting method is disclosed in WO 95/29197.

But, for efficient silane grafting, organic initiators are preferred, such as any one of the peroxide initiators, for example, dicumyl peroxide, di-tert-butyl peroxide, t-butyl perbenzoate, benzoyl peroxide, cumene hydroperoxide, t-butyl peroctoate, methyl ethyl ketone peroxide, 2,5-dimethyl-2,5-di(t-butyl peroxy)hexane, lauryl peroxide, and tert-butyl peracetate. A suitable azo compound is azobisisobutyl nitrite. The amount of initiator can vary, but it is typically present in an amount of at least 0.04, preferably at least 0.06, phr. Typically, the initiator does not exceed 0.15, preferably it does not exceed 0.10, phr. The ratio of silane crosslinker to initiator also can vary widely, but the typical crosslinker:initiator ratio is between about 10:1 and about 30:1, preferably between about 18:1 and about 24:1.

The following examples are provided to further illustrate and illuminate the present invention but are not intended to limit the invention to the specific embodiments set forth.

EXAMPLES

In an investigation to determine the spinnability of various block polymers, several different block polymers were substantially hydrogenated. These block polymers were all triblocks with two vinyl aromatic monomer unit blocks and one conjugated diene monomer unit block (hydrogenated SBS) and were characterized as having varying molecular parameters.

Also included in this investigation was KRATON G 1652 (comparative run 2), a SBS triblock supplied by Shell Chemical Company. The KRATON product is supplied partially hydrogenated. That is, only its conjugated diene monomer unit block is saturated and its vinyl aromatic monomer unit blocks (two polystyrene blocks) remains unchanged. In this investigation, an Instron Capillary Rheometer was used for extrudate strand feed to a variable speed take-up roll. The rheometer die had a diameter of about 1,000 microns and a L/D of 20. The melt temperature was set at 250–255° C. and the output rate was maintained at 0.43 gm/min., unless melt fracture occurred at which time, the melt temperature was increased to 260° C. and output was reduced to 0.14 gm/min. The objective of this investigation was to determine lowest possible denier attainable for each block polymer and collect sample fibers for additional testing. Table 1 provides the molecular parameters, low shear parallel plate viscosity and fiber spinning results for the various block polymers.

TABLE 1

| Example | $M_p$ | $M_w$ | % PS | %1,2 Addition | PS Block $M_w$ | % Conjugated Diene Unit Saturation Level | % Vinyl Aromatic Unit Saturation Level | Parallel Plate Viscosity at 0.1 rad/s, 190° C. (poises) | Minimum Denier |
|---|---|---|---|---|---|---|---|---|---|
| Inv Ex 1 | 62,550 | 62,820 | 30 | 46 | 10,360 | 100 | >95 | 1.10E5 | ~20 |
| Comp 2 | ND | 50,000 | 30 | ND | ND | 100 | <90 | 1.63E6 | None |
| Inv Ex 3 | 67,870 | 67,411 | 35.8 | 39.3 | 12,066 | 100 | >95 | 4.48E5 | ~70 |
| Inv Ex 4 | 81,310 | 80,940 | 32.2 | 39.6 | 13,030 | 100 | >95 | 1.03E6 | ~200* |
| Comp 5 | 81,620 | 81,247 | 37.0 | 39 | 15,030 | 100 | >95 | 8.72E5 | None** |
| Inv Ex 6 | 64,315 | 64,254 | 32.0 | 41.3 | 10,280 | 100 | >95 | 1.92E5 | ~20 |
| Comp 7 | 105,895 | 105,770 | 31.0 | 45 | 16,390 | 100 | >95 | 4.16E6 | None |

ND = not determined.
fiber denier conversion: 20–25 denier = about 60 microns diameter.
% PS and PS Block MW are determined before the hydrogenation step.
*Output rate was adjusted to 0.14 gm/min. and melt temperature was adjusted to 260° C. to offset melt fracture.
**It appeared the suitable fiber could be fabricated at a higher melt temperature (e.g. 260° C.) although such was not attempted in this investigation.

Inventive Example 1 gave excellent fiber spinning results exhibiting a minimum denier of 20. Conversely, comparative run 2 gave poor results. At 0.3 inch/min (0.76 cm/min) of plunger speed (about 0.43 g/min output rate), comparative run 2 exhibited melt fracture. At 0.1 inch/min (0.25 cm/min) of Instron plunger speed, the strand coming out of die was clear and did not have visible melt fracture. Nevertheless, all attempts to start the spinline, even at very low take-up speed, were unsuccessful due to fiber breaks. In fact, fibers could not be even pulled slowly onto the take-up device without breaking the spinline. Thus, it was concluded that fibers of less than about 250 microns could not be made from comparative run 2 using the above-described fiber spinline.

The high molecular weight examples, comparative runs 5 and 7 could not be spun at all at 250–255° C. and about a 0.43 gm/min output rate. In fact, comparative run 7 exhibited severe melt fracture at about 0.43 gm/min, 0.14 gm/min and even at a 0.04 gm/min output rate. The melt-fractured strand coming out of the die broke immediately upon pulling by hand. Note that in contrast, Inventive Example 1 (62,820 $M_w$ and 30 wt. % polystyrene) was spun to a minimum of about 20–25 denier fiber under similar conditions (at 0.43 gm/min output rate).

For fabricating fine denier fibers at melt temperatures less than 260° C. using neat block polymer compositions, Table 1 indicates that the total molecular weight limit is less than or equal to about 81,500 and the molecular weight limit for the vinyl aromatic monomer unit block for a triblock is less than or equal to about 15,000. Nonetheless, it is thought that blending wax, polyolefins, plasticizer, tackifier, processing aid or oil into high molecular weight substantially hydrogenated block copolymers would impart fiber spinnability or melt drawability. That is, it is believed that formulated compositions would show good spinnability and/or melt drawability.

In another investigation, the low shear rheology of Inventive Example 1 and comparative run 2 were measured using a Rheometrics RMS-800 unit. The data from this investigation are shown in FIG. 1. Surprisingly, Inventive Example 1 exhibited dramatically lower low shear viscosity than comparative run 2 even though Inventive Example 1 had a substantially higher molecular weight. The dramatically lower low shear viscosity of Inventive Example 1 is believed to explain its excellent spinnability.

Figure 2:
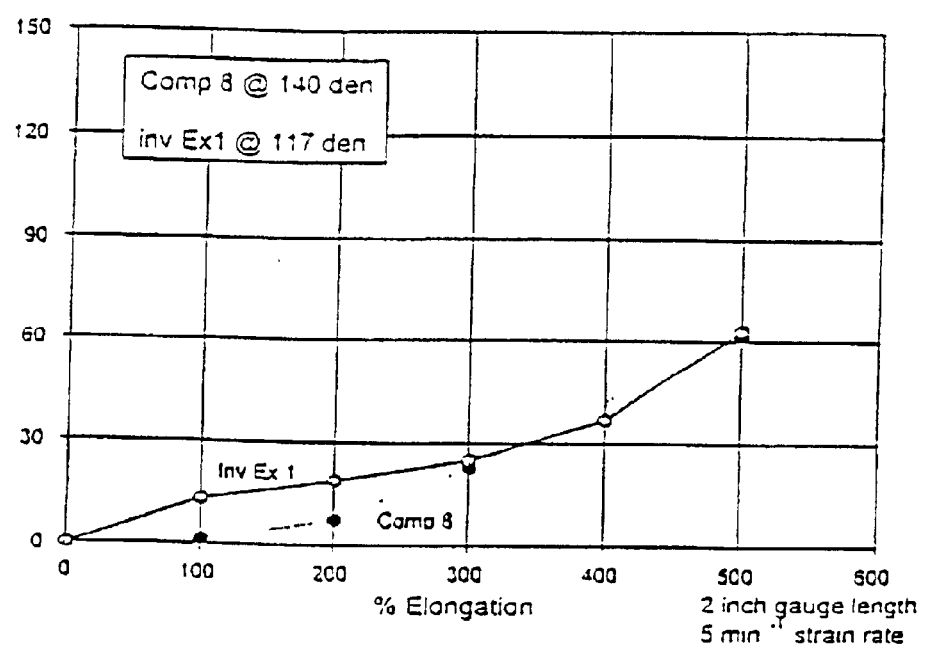
FIG. 2 is a plot of the five cycle percent permanent set at 23° C. for Inventive Example 1 at 117 denier and comparative run 8 at 140 denier.

In a third investigation, the elastic properties of Inventive Example 1 at 117 denier were compared with a 140 denier spandex fiber (comparative run 8) supplied by DuPont Chemical Company under the tradename Lycra*. The investigation consisted of measuring the percent permanent set after a five-cycles at various levels of strain. To determine the percent permanent set, samples of 2 inch (5.28 cm) gauge length of Inventive Example 1 and comparative run 8 were tested using an Instron tensiometer. A crosshead speed of 10 inches/minute (25.4 cm/min) was used to provide a strain rate of 5 $min^{-1}$. Each sample was stretched to a predefined strain (that is, stretched five elongations from 100% to 500% strain at 100% increments using a new samples for each increment) level and then unloaded by reversing the crosshead movement without any hold time in between the stretching and unloading. After five repeats of the same cycle (with no hold time in between the stretching and the unloading), each sample was loaded for a sixth time. The strain at which the load rises above zero was recorded as set strain. The set strain was then plotted as a function of applied strain to provide FIG. 2. FIG. 2 shows that Inventive Example 1 exhibited excellent elastic recovery (low permanent set) after five deformation cycles, especially at higher elongations (strains).

In a fourth investigation, the stick temperatures of Inventive Example 1 and comparative run 2 were determined. Stick temperature was determined by the following method. Two plaques with the dimension of 1 inch.×2 inch×¹⁄₁₆ inch (2.54×5.08×0.16 cm)of the polymer were placed in an oven at different temperatures for 15 min. The stick temperature was recorded as the temperature that the two plaques stuck to each other. The stick temperatures of Inventive Example 1 and comparative run were about 120° C. and 105° C., respectively. Applications where high stick temperatures are an advantage includes elastic fiber used in fabrics subject to high drying temperature, parts of automotive interior, and gaskets.

Figure 3:
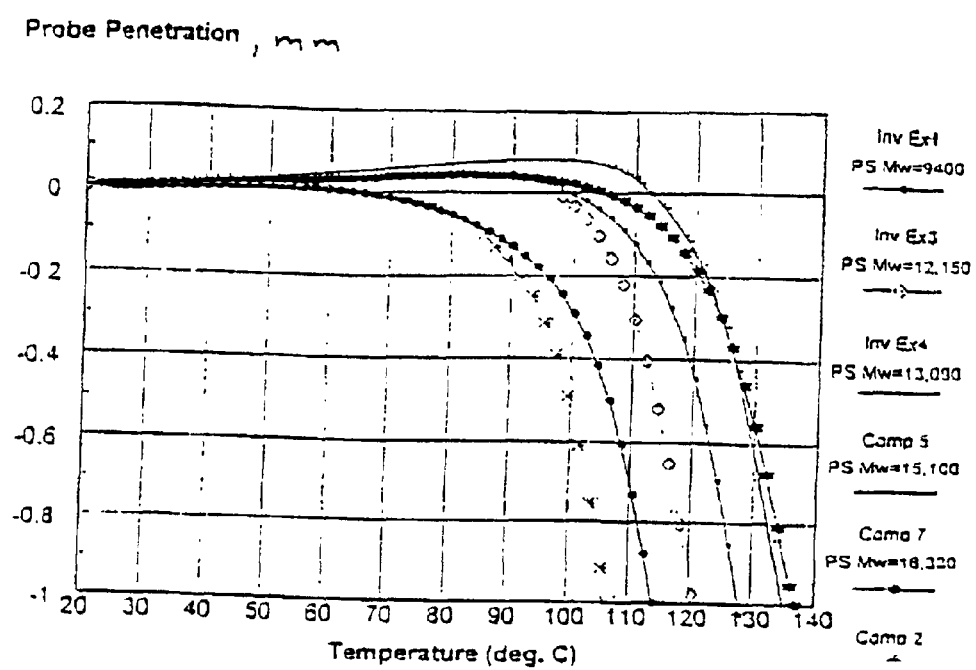
FIG. 3 is a plot of the thermomechanical analysis (TMA) probe penetration data for Inventive Examples 1, 3 and 4 and comparative runs 2, 5 and 7.

In a fifth investigation, the maximum service temperature of Inventive Example 1 and comparative run 2 were determined. Maximum service temperatures were conveniently determined using a thermal mechanical analyzer (Perkin-Elmer TMA 7 series). Samples of each block polymer were scanned at 5° C./minute with the load set at 1 Newton. The point at which the TMA probe penetrated 1 mm into the sample was taken as the maximum service temperature for the sample. The TMA probe penetration data from the investigation is shown in FIG. 3. The data show that Inventive Example 1 exhibited higher heat resistance (i.e. had a higher maximum service temperature) than comparative run 2.

In another evaluation, the effect of formulating block polymers with oil was investigated. In this evaluation, white mineral oil (Witco 200 process oil supplied by Witco Chemical Corporation) was separately melt compounded with comparative block polymer 2 and with a substantially hydrogenated triblock polymer (Inventive Example 9) characterized as having a $M_p$ of 65,900 and comprising 32 weight percent polystyrene before hydrogenated and which was hydrogenated 100 percent with respect to its conjugated diene unit (butadiene) and >99 weight percent with respect to its vinyl aromatic units (styrene). The oil was added at 12, 24 and 36 weight percent into both block polymers and the resulting formulated systems as well as the neat block polymers themselves were all tested for various performance properties, including ultimate tensile strength, melt flow rate at 200° C. using a 5-kg weight, percent set and percent stress relaxation.

The tensile properties (ultimate tensile strength and percent elongation) were determined in accordance with ASTM denier, 70 denier fiber was used for the testing. The 70 denier fiber for each sample was made using a capillary rheometer as described above. Notably, fiber cannot be spun at 40 wt. % Kraton G1652.

Figure 5:
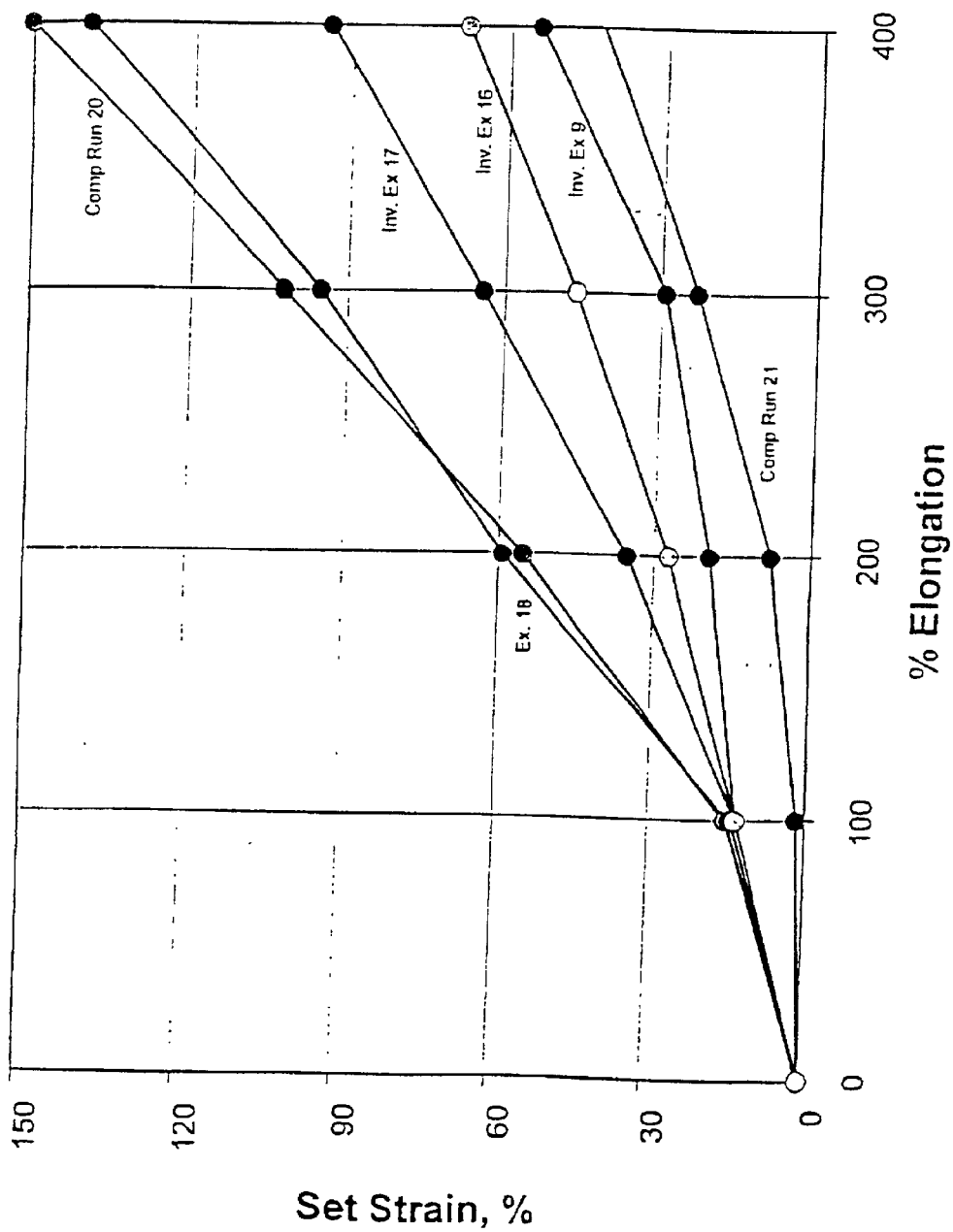
FIG. 5 is a plot of percent set strain versus percent elongation for Inventive Examples 9, 16 and 17, Example 18 and comparative runs 20 and 21.
Figure 6:
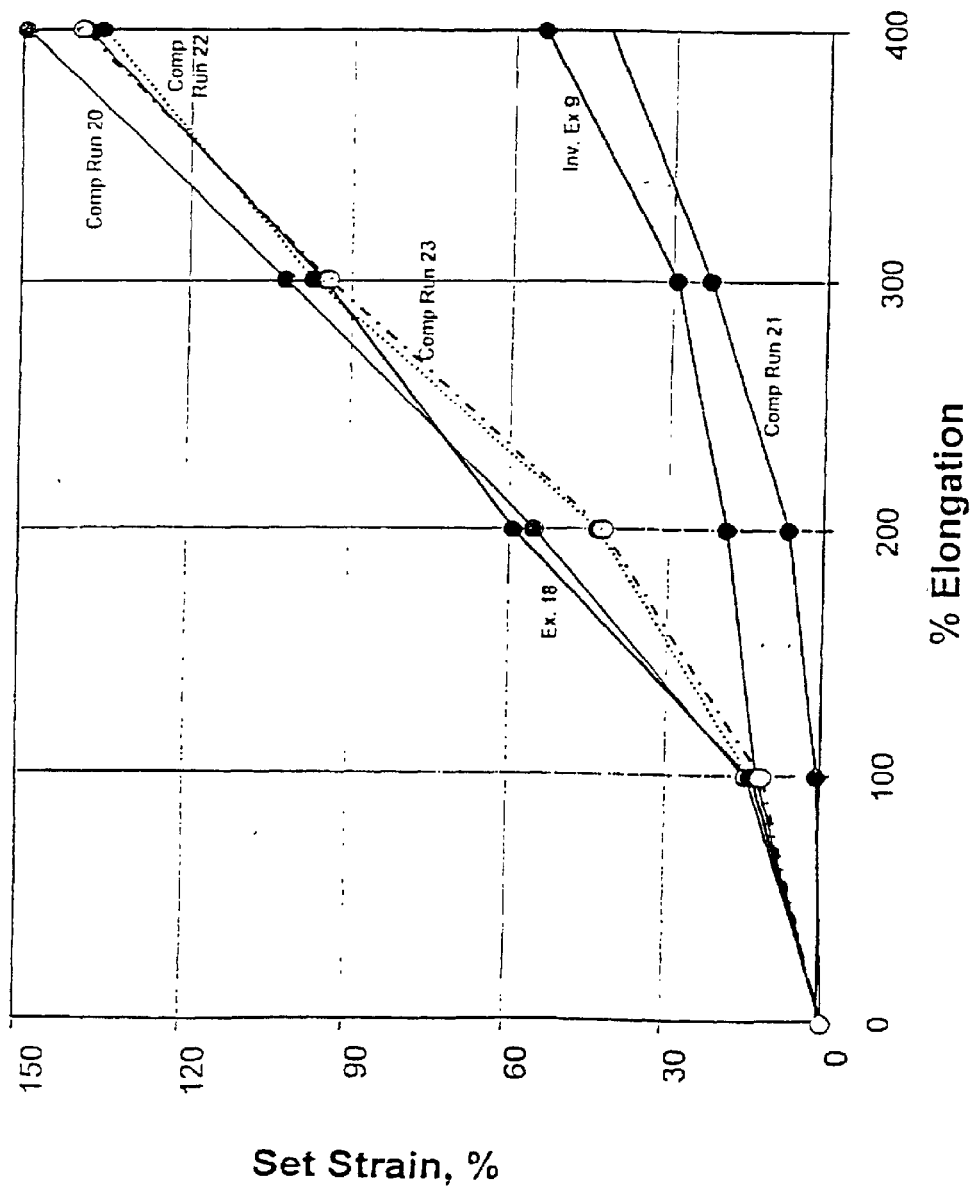
FIG. 6 is a plot of percent set strain versus percent elongation for Inventive Example 9, Example 18 and comparative runs 20–23.
Figure 7:
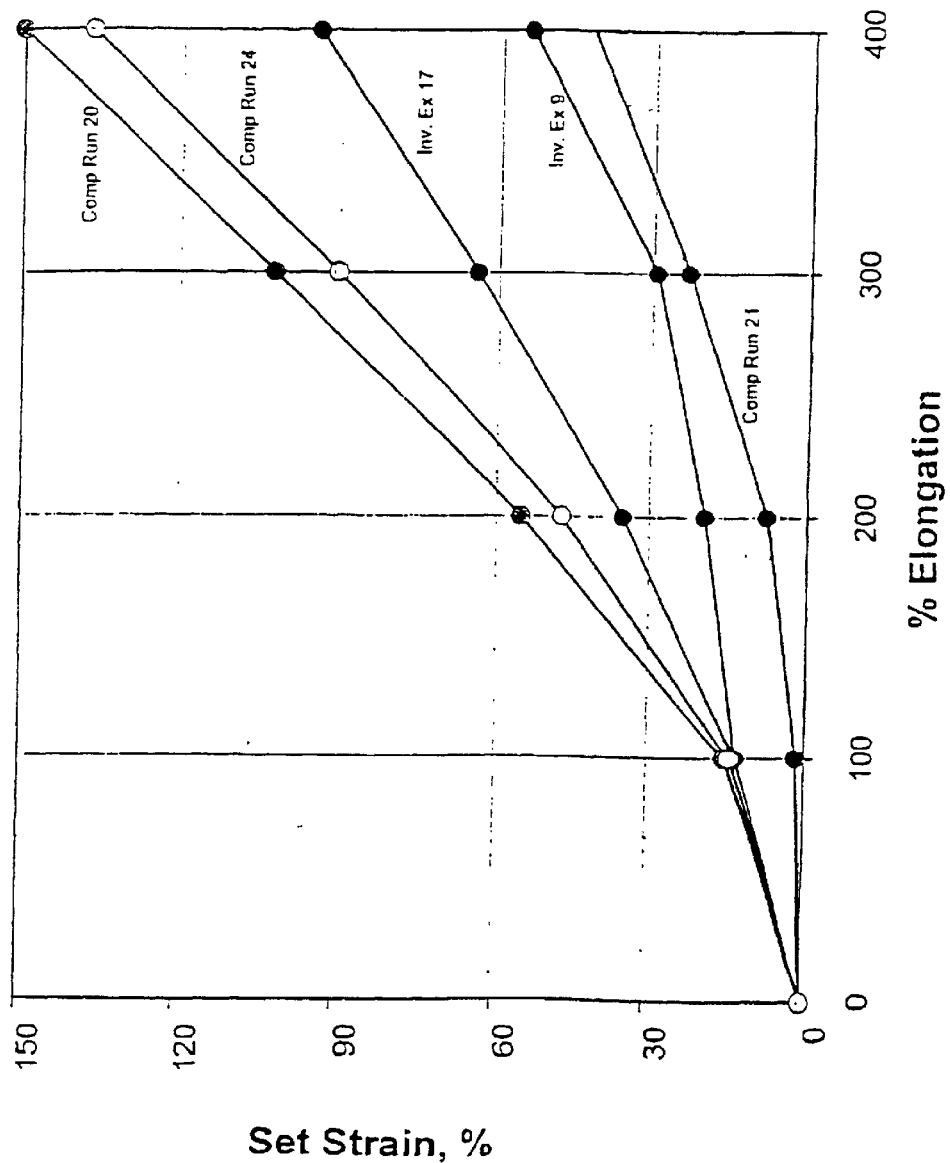
FIG. 7 is a plot of percent set strain versus percent elongation for Inventive Examples 9 and 17 and comparative runs 20, 21 and 24.

FIGS. 5–7 show the results of this blend evaluation. Additive weight percent calculations from the results in these figures indicate that at 200%–300% strain, ethylene polymer blends containing greater than or equal to 40 weight percent substantially hydrogenated block copolymer exhibited surprisingly better elasticity than is predictable from additive weight percent calculations. Also, the improvement in elasticity at greater than or equal to 40 weight percent was substantially better than was predictable from results at lower blend levels or from results at equivalent blend levels with partially hydrogenated block copolymers.

TABLE 2

| Example | Block Polymer | Weight Percent Oil | MFR (g/10 min) | Shore A | Ultimate Tensile (psi) | 300% Modulus (psi) | Percent Elongation | 1 Cycle % set | 1 Cycle % stress relax | 2 Cycle % set | 2 Cycle % stress relax |
|---|---|---|---|---|---|---|---|---|---|---|---|
| Inv. Ex 9 | Inv. Ex 9 | 0 | 4.5 | 81.5 | 5,979 | 1,194 | 450 | | | | |
| Inv. Ex 10 | Inv. Ex 9 | 12 | 26.3 | 57.0 | 5154 | 646 | 583 | 6 | 8.7 | 8.5 | 5.8 |
| Inv. Ex 11 | Inv. Ex 9 | 24 | 124.2 | 54.0 | 3674 | 395 | 700 | 7.8 | 8.2 | 10.6 | 5.2 |
| Inv. Ex 12 | Inv. Ex 9 | 36 | 512.2 | 52.5 | 474 | 227 | 881 | 15.2 | 10.7 | 22.5 | 7.2 |
| Comp Run 2 | Comp Run 2 | 0 | 0.9 | 78.8 | 5,651 | 1,003 | 481 | | | | |
| Comp Run 13 | Comp Run 2 | 12 | 5.3 | 59.5 | 4608 | 704 | 606 | 8.1 | 8.3 | 8.8 | 6.3 |
| Comp Run 14 | Comp Run 2 | 24 | 30.6 | 56.5 | 2465 | 459 | 694 | 6.3 | 6.9 | 7.4 | 5.3 |
| Comp Run 15 | Comp Run 2 | 36 | 157.4 | 52.6 | 1307 | 355 | 706 | 6.9 | 7.4 | 9.2 | 5.3 |

D-638. The melt flow rates were determined in accordance with ASTM D-1238, Condition 200° C./5 kg. The Shore A values were determined in accordance with ASTM D-2240. Modulus was determined in accordance with ASTM D-790. Percent haze values were determined in accordance with ASTM D-1003.The percent stress relaxation and set data were determined using an Instron 1123 tensiometer. In this determination (which is based on ASTM D 4649-87, Appendix A 13), samples were stretched to 200% elongation at a crosshead speed of 1 in/min (2.54 cm/min) and held there for 30 seconds for the stress relaxation measurement. The crosshead was then returned (unloaded) at 10 in./min. (25.4 cm/min) and after 60 seconds the set was measured. Data were collected for one and two complete cycles.

Figure 4:
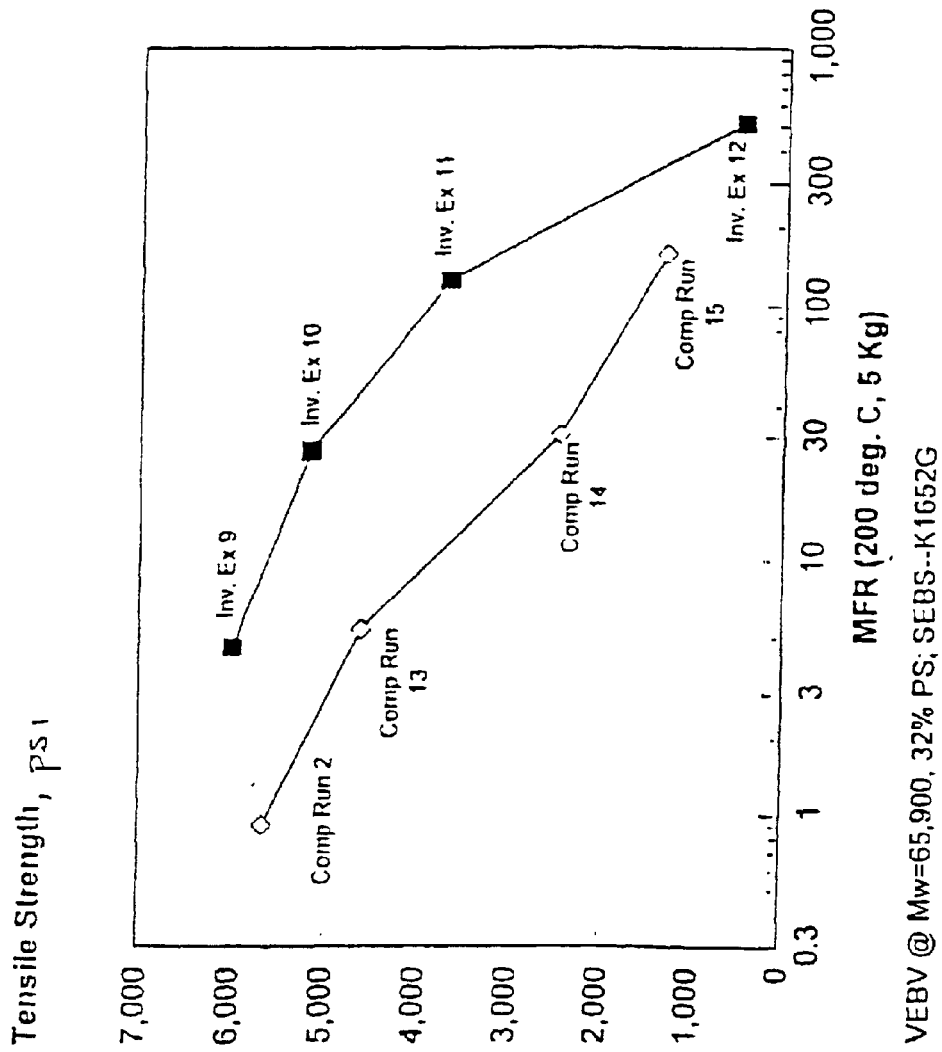
FIG. 4 is a plot of tensile strength (in psi) versus melt flow rate at 200° C./5 kg (in g/10 minutes) for Inventive Examples 9–12 and comparative runs 2 and 13–15.

Table 2 shows the designations of the various formulated systems and the results of the performance testing. FIG. 4, which is a plot of the interrelationship between the melt flow rate and ultimate tensile strength for the various examples, shows surprisingly results for the inventive composition (Inventive Example 9) and the inventive formulated systems (Inventive Examples 10–12). The inventive composition and inventive formulated systems show excellent strength to processability performance.

In another evaluation, the effect of blending a substantially hydrogenated block copolymer and a partially hydrogenated block copolymer into an ethylene polymer was investigated. Table 3 lists the various the blends investigated in this evaluation and includes the block polymer weight percentages and example designations. The ethylene polymer was a substantially linear ethylene interpolymer supplied by Dupont-Dow Elastomers under the designation ENGAGE™ EG8200. Lycra was also included in this evaluation as a control material. The various blends and control samples were tested for percent elongation and percent set strain at five cycles as described above, except the range was from 100% to 400% strain instead of from 100% to 500%. In this evaluation, except for Lycra which was tested at 140

TABLE 3

| Example | Weight Percent SHBP | Weight Percent EG8200 | Weight Percent PHBP |
|---|---|---|---|
| Inv. Ex 9 | 100 | 0 | 0 |
| Inv. Ex 16 | 60 | 40 | 0 |
| Inv. Ex 17 | 40 | 60 | 0 |
| Ex 18 | 20 | 80 | 0 |
| Comp Run 20 | 0 | 100 | 0 |
| Comp Run 21* | 0 | 0 | 0 |
| Comp Run 22† | 0 | 80 | 20 |
| Comp Run 23** | 0 | 80 | 20 |
| Comp Run 24† | 0 | 60 | 40 |

*comparative run 21 is Lycra and the same as comparative run 8
SHBP = substantially hydrogenated block copolymer (i.e. Inventive Example 9).
PHBP = partially hydrogenated block copolymer.
†The partially hydrogenated block copolymer was Kraton G1657 supplied by Shell Chemical Company.
**The partially hydrogenated block copolymer was Kraton G1652 supplied by Shell Chemical Company.

What is claimed is:

1. A fiber produced from a composition comprising at least one hydrogenated block copolymer and at least one other polymer selected from the group consisting of a reactive tailored liquid polyurethane, an elastomeric or sulfonated ethylene/vinyl aromatic interpolymer, an elastomeric ethylene/C3–C20 α-olefin interpolymer, an C3–C20 α-olefin/conjugated diene interpolymer, an elastic polypropylene polymer, an enhanced polypropylene polymer, an elastomeric thermoplastic polyurethane, an elastic polyester, a partially hydrogenated block copolymer, an elastic polyamide, a hydroxyl functionalized polyether (or polyetheramine), a styrene/conjugated diene interpolymer, and an elastomeric metallocene-catalyzed synthetic polymer or a blend or formulated system thereof, wherein the hydrogenated block copolymer is a substantially hydrogenated block copolymer characterized as having:
   i) a weight ratio of conjugated diene monomer unit block to vinyl aromatic monomer unit block before hydrogenation of greater than or equal to 60:40;
   ii) a weight average molecular weight (Mw) before hydrogenation of from about 30,000 to about 150,000, wherein each vinyl aromatic monomer unit block (a) has a weight average molecular weight, Mwa, of from about 5,000 to about 45,000 and each conjugated diene monomer unit block (b) has a weight average molecular weight, Mwb, of from about 12,000 to about 110,000; and
   iii) a hydrogenation level such that each vinyl aromatic monomer unit block is hydrogenated to a level of greater than 90 percent and each conjugated diene monomer unit block is hydrogenated to a level of greater than 95 percent, as determined using UV-VIS spectrophotometry and proton NMR analysis.

2. A composite having a nonwoven portion comprising the fiber of claim 1.

3. The composite of claim 2, which comprises leg gathers, leg bands, sidepanels or a waistband.

4. A fabric, thread, filament, ribbon or fibrous web comprising the fiber of claim 1.

5. A nonwoven strip or ribbon comprising the fiber of claim 1.

6. The fiber of claim 1 wherein the fiber is monofilament, bicomponent or multicomponent.

7. The fiber of claim 1, wherein the fiber is surface treated or crosslinked.

8. A core/sheath structure comprising the fiber of claim 1.

9. A composite structure comprising the fiber of claim 1.

10. An absorbent item comprising the fiber of claim 1.

11. A nonwoven item comprising the fiber of claim 1.

12. An apparel accessory item comprising the fiber of claim 1.

13. The accessory item of claim 12, wherein the item is a belt, sock, ribbon, headband, or hat.

14. A woven or knitted item comprising the fiber of claim 1.

15. A carpet comprising the fiber of claim 1.

16. A diaper comprising the fiber of claim 1.

17. A incontinence pad comprising the fiber of claim 1.

18. A sanitary napkin comprising the fiber of claim 1.

19. A yarn comprising the fiber of claim 1.

20. A textile item comprising the fiber of claim 1.

21. The fiber of claim 1, wherein fiber thickness is in the range of from about 0.1 micron to about 24 mils.

22. The fiber of claim 1, wherein the at least one other polymeric material is a homogeneously branched ethylene polymer.

23. The fiber of claim 1, wherein the substantially hydrogenated block copolymer is a triblock having, before hydrogenation, two vinyl aromatic monomer unit blocks and one conjugated diene monomer unit block.

24. The fiber of claim 1, wherein each vinyl aromatic monomer unit block has a weight average molecular weight less than or equal to 15,000.

25. The fiber of claim 1, wherein at least one of the vinyl aromatic monomer unit blocks comprises styrene.

26. The elastic article of claim 1, wherein the conjugated diene monomer unit block is butadiene.

* * * * *